United States Patent [19]
Caprathe et al.

[11] Patent Number: 6,001,331
[45] Date of Patent: Dec. 14, 1999

[54] METHOD OF IMAGING AMYLOID DEPOSITS

[75] Inventors: Bradley W. Caprathe, Livonia; John L. Gilmore; Sheryl J. Hays, both of Ann Arbor; Juan C. Jaen, Plymouth; Harry LeVine, III, Ann Arbor, all of Mich.

[73] Assignee: Warner-Lambert Company, Morris Plains, N.J.

[21] Appl. No.: 09/117,101

[22] PCT Filed: Jan. 2, 1997

[86] PCT No.: PCT/US97/00251

§ 371 Date: Jul. 22, 1998

§ 102(e) Date: Jul. 22, 1998

[87] PCT Pub. No.: WO97/26919

PCT Pub. Date: Jul. 31, 1997

Related U.S. Application Data

[60] Provisional application No. 60/010,495, Jan. 24, 1996.

[51] Int. Cl.$^6$ .......................... A61K 49/00; G01N 31/00; G01N 33/48
[52] U.S. Cl. ...................... 424/9.1; 424/1.11; 424/1.65; 424/1.81; 424/1.85; 548/400; 536/102; 536/123.1
[58] Field of Search ................... 424/1.11, 1.65, 424/1.81, 1.85, 1.73, 9.1; 548/400; 536/123.1, 18.7, 107, 102; 106/206.1, 216.1, 145.1, 207.5; 514/23; 127/28, 22, 59, 25; 527/300

[56] References Cited

U.S. PATENT DOCUMENTS

| | | | |
|---|---|---|---|
| 2,149,051 | 2/1939 | Heinrich et al. | 260/158 |
| 2,785,151 | 3/1957 | Gorin et al. | 260/96.5 |
| 2,785,154 | 3/1957 | Locke et al. | 260/114 |
| 4,145,114 | 3/1979 | Coates et al. | 350/349 |
| 4,454,107 | 6/1984 | Rolleston . | |
| 4,919,915 | 4/1990 | Averback . | |
| 4,933,156 | 6/1990 | Quay et al. . | |
| 5,008,099 | 4/1991 | Quay et al. . | |
| 5,039,511 | 8/1991 | Quay et al. . | |
| 5,434,050 | 7/1995 | Maggio et al. . | |

FOREIGN PATENT DOCUMENTS

| | | |
|---|---|---|
| 2090274 | of 0000 | United Kingdom . |
| 2223578A | 4/1990 | United Kingdom . |
| 9304194 | 3/1993 | WIPO . |
| 9401116 | 1/1994 | WIPO . |
| 9422437 | 10/1994 | WIPO . |
| 9425029 | 11/1994 | WIPO . |
| 9427614 | 12/1994 | WIPO . |
| 9428412 | 12/1994 | WIPO . |
| 9504538 | 2/1995 | WIPO . |
| 9506469 | 3/1995 | WIPO . |
| 9512815 | 5/1995 | WIPO . |

OTHER PUBLICATIONS

Hartmann, H., et al., "Nucleophilic substitution on Arylazo Compounds: Part IV. Reactions of Chloro–Substituted Arylazonaphthalenes with Primary and Secondary Amines". Dyes and Pigments, 1991, vol. 16, No. 2, pp. 119–136.

Cuadro, A., et al., "Styryl and Azastyryl 1,3–Benzazoles with Antihelmitic Activity". Il Farmaco, 1992, vol. 47, No. 4, pp. 477–488.

Peters, A.T., et al., "5,6–(6,7–)Dichlorobenzothiazolylazo Dyes for Synthetic–Polymer Fibers". Dyes and Pigments, 1992, vol. 18, No. 2, pp. 115–123.

LeVine, III, Harry., "Thioflavine T interaction with synthetic Alzheimer's disease β–amyloid peptides: Detection of amyloid aggregation in solution". Protein Science, 1993, vol. 2, pp. 404–410.

Kuramoto, Nobuhiro. "Syntheses of Amphiphilic Benzothiazolium Azo Dyes and Behavior of their Monolayers on a Water Surface". Dyes and Pigments, 1993, vol. 21, No. 3, pp. 159–171.

Klunk, William E., et al., "Development of Small Molecule Probes for the Beta–Amyloid Protein of Alzheimer's Disease", Neurobiology of Aging, 1994, vol. 15, No. 6, pp. 691–698.

Klunk, William E., et al., "Chrysamine–G Binding to Alzheimer and Control Brain: Autopsy Study of a New Amyloid Probe", Neurobiology of Aging, 1995, vol. 16, No. 4, pp. 541–548.

*Primary Examiner*—Jose' G. Dees
*Assistant Examiner*—Dameron Jones
*Attorney, Agent, or Firm*—Charles W. Ashbrook

[57] ABSTRACT

The present invention provides a method of imaging amyloid deposits and radiolabeled compounds useful in imaging amyloid deposits. The invention also provides a method of delivering a therapeutic agent to amyloid deposits, a method of inhibiting the aggregation of amyloid proteins to form amyloid deposits, and a method of determining a compound's ability to inhibit aggregation of amyloid proteins.

17 Claims, No Drawings

METHOD OF IMAGING AMYLOID DEPOSITS

This application claims the benefit of U.S. Provisional Application No. 60/010,495 filed Jan. 24, 1996.

FIELD OF THE INVENTION

This invention relates to a method of imaging amyloid deposits and to labeled compounds useful in imaging amyloid deposits. This invention also relates to a method of delivering a therapeutic agent to amyloid deposits, a method of inhibiting the aggregation of amyloid proteins to form amyloid deposits, and a method of determining a compound's ability to inhibit aggregation of amyloid proteins.

BACKGROUND OF THE INVENTION

Amyloidosis is a condition characterized by the accumulation of various insoluble, fibrillar proteins in the tissues of a patient. The fibrillar proteins that comprise the accumulations or deposits are called amyloid proteins. While the particular proteins or peptides found in the deposits vary, the presence of fibrillar morphology and a large amount of β-sheet secondary structure is seen in many types of amyloids. An amyloid deposit is formed by the aggregation of amyloid proteins, followed by the further combination of aggregates and/or amyloid proteins.

The presence of amyloid deposits has been shown in various diseases such as Mediterranean fever, Muckle-Wells syndrome, idiopathic myeloma, amyloid polyneuropathy, amyloid cardiomyopathy, systemic senile amyloidosis, amyloid polyneuropathy, hereditary cerebral hemorrhage with amyloidosis, Alzheimer's disease, Down's syndrome, Scrapie, Creutzfeldt-Jacob disease, Kuru, Gerstamnn-Straussler-Scheinker syndrome, medullary carcinoma of the thyroid, Isolated atrial amyloid, $\beta_2$-microglobulin amyloid in dialysis patients, inclusion body myositis, $\beta_2$-amyloid deposits in muscle wasting disease, and Islets of Langerhans diabetes Type II insulinoma.

Thus, a simple, noninvasive method for detecting and quantitating amyloid deposits in a patient has been eagerly sought. Presently, detection of amyloid deposits involves histological analysis of biopsy or autopsy materials. Both methods have major drawbacks. For example, an autopsy can only be used for a postmortem diagnosis.

The direct imaging of amyloid deposits in vivo is difficult, as the deposits have many of the same physical properties (i.e., density and water content) as normal tissues. Attempts to image amyloid deposits using magnetic resonance imaging (MRI) and computer-assisted tomography (CAT) have been disappointing and have detected amyloid deposits only under certain favorable conditions. In addition, efforts to label amyloid deposits with antibodies, serum amyloid P protein, or other probe molecules has provided some selectivity on the periphery of tissues, but has provided for poor imaging of tissue interiors.

Thus, it would be useful to have a noninvasive technique for imaging and quantitating amyloid deposits in a patient. In addition, it would be useful to have compounds that inhibit the aggregation of amyloid proteins to form amyloid deposits and a method for determining a compound's ability to inhibit amyloid protein aggregation.

SUMMARY OF THE INVENTION

The present invention provides a method of imaging amyloid deposits, the method comprising introducing into a patient a detectable quantity of a labeled compound having the Formula I or a pharmaceutically acceptable salt, ester, amide, or prodrug thereof

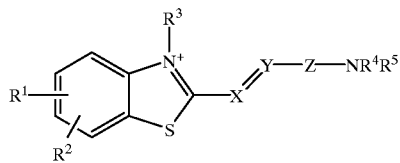

wherein
X and Y are each independently C or N and the X=Y double bond has the trans configuration;
Z is

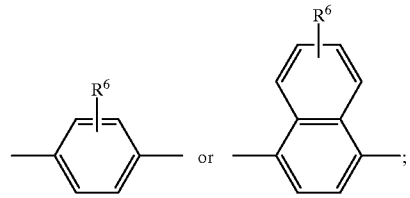

$R^1$ and $R^2$ are each independently hydrogen, $C_1$–$C_6$ alkyl, $C_1$–$C_6$ alkoxy, hydroxy, halogen, amino, di($C_1$–$C_6$ alkyl)amino, mono($C_1$–$C_6$ alkyl)amino, nitro, $C_1$–$C_6$ thioalkoxy, or $R^1$ and $R^2$ combined form a benzene, cyclopentane, or cyclohexane ring that is fused to the phenyl ring;

$R^3$ is a lone pair of electrons, $C_1$–$C_{10}$ alkyl, $C_2$–$C_{10}$ alkenyl, arylalkyl, (heteroaryl)alkyl, (cycloalkyl)alkyl, arylalkenyl, diarylalkyl or —$(CH_2)_m$—A—$(CH_2)_n$—Q;

m is 1 to 6 and n is 0 to 6;

A is —O—, —S—, —$NR^{4-}$, C=O, or a single bond;

Q is phenyl substituted with $R^7$ or naphthyl substituted with $R^7$;

$R^7$ is hydrogen, $C_1$–$C_6$ alkyl, $C_1$–$C_6$ alkoxy, hydroxy, halogen, amino, di($C_1$–$C_6$ alkyl)amino, nitro, $C_1$–$C_6$ thioalkoxy, aryl, heteroaryl, aryloxy, —CO-aryl, or arylthio;

$R^4$ and $R^5$ are each independently hydrogen, $C_1$–$C_6$ alkyl or —$NR^4R^5$ represents a 5-, 6- or 7-membered ring containing nitrogen; and $R^6$ is hydrogen, $C_1$–$C_6$ alkyl, $C_1$–$C_6$ alkoxy, hydroxy, halogen, amino, di($C_1$–$C_6$ alkyl)amino, nitro, or $C_1$–$C_6$ thioalkoxy; allowing sufficient time for the labeled compound to become associated with amyloid deposits; and detecting the labeled compound associated with the amyloid deposits.

In a preferred embodiment of the compound having Formula I, X=Y is C=C or N=N;

$R^1$ and $R^2$ are each independently hydrogen, $C_1$–$C_6$ alkyl, $C_1$–$C_6$ alkoxy, halogen, nitro, $C_1$–$C_6$ thioalkoxy, or $R^1$ and $R^2$ combined form a benzene, cyclopentane or cyclohexane ring that is fused to the phenyl ring;

$R^3$ is $C_1$–$C_{10}$ alkyl, $C_2$–$C_{10}$ alkenyl, arylalkyl, (cycloalkyl)alkyl, arylalkenyl, diarylalkenyl, or —$(CH_2)_m$—A—$(CH_2)_n$—Q;

m is 1 to 5 and n is 0 to 4;

A is —O—, —S—, or a single bond;

Q is phenyl substituted with $R^7$ or naphthyl substituted with $R^7$;

$R^7$ is hydrogen, $C_1$–$C_6$ alkyl, $C_1$–$C_6$ alkoxy, hydroxy, halogen, amino, di($C_1$–$C_6$ alkyl)amino, nitro, $C_1$–$C_6$ thioalkoxy, aryl, aryloxy, —CO-aryl, or arylthio;

$R^4$ and $R^5$ are each independently hydrogen or $C_1$–$C_6$ alkyl; and $R^6$ is hydrogen, $C_1$–$C_6$ alkyl, or halogen.

In another preferred embodiment of the compound having Formula I, X=Y is C=C or N=N;

$R^1$ and $R^2$ are each independently hydrogen, $C_1$–$C_6$ alkyl, $C_1$–$C_6$ alkoxy, halogen, nitro, or $R^1$ and $R^2$ combined form a (4,5), (5,6), or (6,7) benzene ring that is fused to the phenyl ring;

$R^3$ is $C_1$–$C_{10}$ alkyl, $C_2$–$C_{10}$ alkenyl, arylalkyl, arylalkenyl, diarylalkyl, or —(CH$_2$)$_m$—A—(CH$_2$)$_n$—Q;

m is 2 to 4 and n is 0 to 3;

A is —O—, or a single bond;

Q is phenyl substituted with $R^7$ or naphthyl substituted with $R^7$;

$R^7$ is hydrogen, $C_1$–$C_6$ alkyl, $C_1$–$C_6$ alkoxy, hydroxy, halogen, aryl, aryloxy, or —CO-aryl;

$R^4$ and $R^5$ are each independently hydrogen, methyl, ethyl, n-propyl or n-butyl; and $R^6$ is hydrogen or halogen.

In another aspect, the present invention provides a method of delivering a therapeutic agent to an amyloid deposit comprising introducing into a patient a compound having the formula

A—B—C or a pharmaceutically acceptable salt, ester, amide, or prodrug thereof, wherein A is

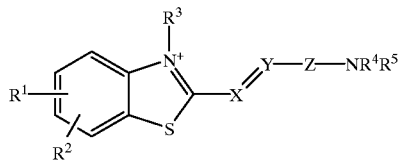

X and Y are each independently C or N and the X=Y double bond has the trans configuration;

Z is

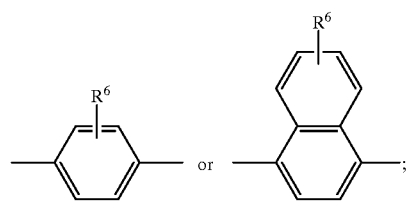

$R^1$ and $R^2$ are each independently hydrogen, $C_1$–$C_6$ alkyl, $C_1$–$C_6$ alkoxy, hydroxy, halogen, amino, di($C_1$–$C_6$ alkyl)amino, mono($C_1$–$C_6$ alkyl)amino, nitro, $C_1$–$C_6$ thioalkoxy or $R^1$ and $R^2$ combined form a benzene, cyclopentane, or cyclohexane ring that is fused to the phenyl ring;

$R^3$ is a lone pair of electrons, $C_1$–$C_{10}$ alkyl, $C_2$–$C_{10}$ alkenyl, arylalkyl, (heteroaryl)alkyl, (cycloalkyl)alkyl, arylalkenyl, diarylalkyl or —(CH$_2$)$_m$—A—(CH$_2$)$_n$—Q;

m is 1 to 6 and n is 0 to 6;

A is —O—, —S—, —NR$^4$-, C=O, or a single bond;

Q is phenyl substituted with $R^7$ or naphthyl substituted with $R^7$;

$R^7$ is hydrogen, $C_1$–$C_6$ alkyl, $C_1$–$C_6$ alkoxy, hydroxy, halogen, amino, di($C_1$–$C_6$ alkyl)amino, nitro, $C_1$–$C_6$ thioalkoxy, aryl, heteroaryl, aryloxy, —CO-aryl or arylthio;

$R^4$ and $R^5$ are each independently hydrogen, $C_1$–$C_6$ alkyl or —NR$^4$R$^5$ represents a 5-, 6-, or 7-membered ring containing nitrogen; and $R^6$ is hydrogen, $C_1$–$C_6$ alkyl, $C_1$–$C_6$ alkoxy, hydroxy, halogen, amino, di($C_1$–$C_6$ alkyl)amino, nitro or $C_1$–$C_6$ thioalkoxy;

B is a linking moiety or a bond; and

C is a therapeutic agent.

The present invention also provides a method of inhibiting the aggregation of amyloid proteins to form amyloid deposits, the method comprising administering to a patient an amyloid protein aggregation inhibiting amount of a compound of Formula I or a pharmaceutically acceptable salt, ester, amide, or prodrug thereof

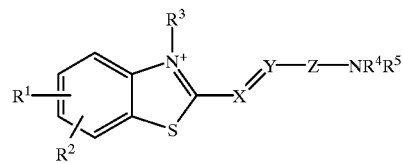

wherein

X and Y are each independently C or N and the X=Y double bond has the trans configuration;

Z is

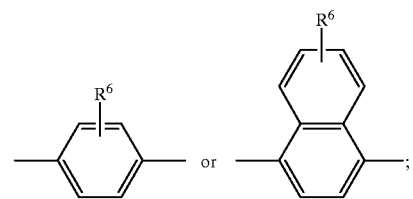

$R^1$ and $R^2$ are each independently hydrogen, $C_1$–$C_6$ alkyl, $C_1$–$C_6$ alkoxy, hydroxy, halogen, amino, di($C_1$–$C_6$ alkyl)amino, mono($C_1$–$C_6$ alkyl)amino, nitro, $C_1$–$C_6$ thioalkoxy or $R^1$ and $R^2$ combined form a benzene, cyclopentane, or cyclohexane ring that is fused to the phenyl ring;

$R^3$ is a lone pair of electrons, $C_1$–$C_{10}$ alkyl, $C_2$–$C_{10}$ alkenyl, arylalkyl, (heteroaryl)alkyl, (cycloalkyl)alkyl, arylalkenyl, diarylalkyl, or —(CH$_2$)$_m$—A—(CH$_2$)$_n$—Q;

m is 1 to 6 and n is 0 to 6;

A is —O—, —S—, —NR$^4$, C=O, or a single bond;

Q is phenyl substituted with $R^7$ or naphthyl substituted with $R^7$;

$R^7$ is hydrogen, $C_1$–$C_6$ alkyl, $C_1$–$C_6$ alkoxy, hydroxy, halogen, amino, di($C_1$–$C_6$ alkyl)amino, nitro, $C_1$–$C_6$ thioalkoxy, aryl, heteroaryl, aryloxy, —CO-aryl, or arylthio;

$R^4$ and $R^5$ are each independently hydrogen, $C_1$–$C_6$ alkyl or —NR$^4$R$^5$ represents a 5-, 6- or 7-membered ring containing nitrogen; and $R^6$ is hydrogen, $C_1$–$C_6$ alkyl, $C_1$–$C_6$ alkoxy, hydroxy, halogen, amino, di($C_1$–$C_6$ alkyl)amino, nitro, or $C_1$–$C_6$ thioalkoxy.

The present invention also provides a method for determining a compound's ability to inhibit the aggregation of amyloid proteins, the method comprising combining solutions of the compound with amyloid proteins under conditions that are known to lead to amyloid protein aggregation; introducing into the solution a labeled compound of Formula I or a pharmaceutically acceptable salt, ester, amide, or prodrug thereof

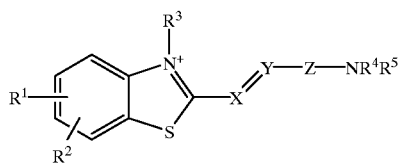

I wherein

X and Y are each independently C or N and the X═Y double bond has the trans configuration;

Z is

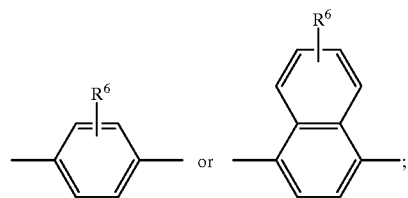

$R^1$ and $R^2$ are each independently hydrogen, $C_1$–$C_6$ alkyl, $C_1$–$C_6$ alkoxy, hydroxy, halogen, amino, di($C_1$–$C_6$ alkyl)amino, mono($C_1$–$C_6$ alkyl)amino, nitro, $C_1$–$C_6$ thioalkoxy, or $R^1$ and $R^2$ combined form a benzene, cyclopentane, or cyclohexane ring that is fused to the phenyl ring;

$R^3$ is a lone pair of electrons, $C_1$–$C_{10}$ alkyl, $C_2$–$C_{10}$ alkenyl, arylalkyl, (heteroaryl)alkyl, (cycloalkyl)alkyl, arylalkenyl, diarylalkyl, or —($CH_2$)$_m$—A—($CH_2$)$_n$—Q;

m is 1 to 6 and n is 0 to 6;

A is —O—, —S—, —$NR^{4+}$, C═O, or a single bond;

Q is phenyl substituted with $R^7$ or naphthyl substituted with $R^7$;

$R^7$ is hydrogen, $C_1$–$C_6$ alkyl, $C_1$–$C_6$ alkoxy, hydroxy, halogen, amino, di($C_1$–$C_6$ alkyl)amino, nitro, $C_1$–$C_6$ thioalkoxy, aryl, heteroaryl, aryloxy, —CO-aryl, or arylthio;

$R^4$ and R5 are each independently hydrogen, $C_1$–$C_6$ alkyl or —$NR^4R^5$ represents a 5-, 6- or 7-membered ring containing nitrogen; and $R^6$ is hydrogen, $C_1$–$C_6$ alkyl, $C_1$–$C_6$ alkoxy, hydroxy, halogen, amino, di($C_1$–$C_6$ alkyl)amino, nitro, or $C_1$–$C_6$ thioalkoxy; filtering or centrifuging the solution; and determining the amount of labeled compound in the filtrate or supernatant.

Also provided is a compound of the Formula I or a pharmaceutically acceptable salt, ester, amide, or prodrug thereof

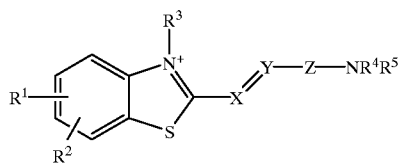

I wherein

X and Y are each independently C or N and the X═Y double bond has the trans configuration;

Z is

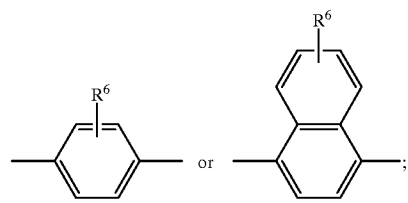

$R^1$ and $R^2$ are each independently hydrogen, $C_1$–$C_6$ alkyl, $C_1$–$C_6$ alkoxy, hydroxy, halogen, amino, di($C_1$–$C_6$ alkyl)amino, mono($C_1$–$C_6$ alkyl)amino, nitro, $C_1$–$C_6$ thioalkoxy, or $R^1$ and $R^2$ combined form a benzene, cyclopentane, or cyclohexane ring that is fused to the phenyl ring;

$R^3$ is a lone pair of electrons, $C_1$–$C_{10}$ alkyl, $C_2$–$C_{10}$ alkenyl, arylalkyl, (heteroaryl)alkyl, (cycloalkyl)alkyl, arylalkenyl, diarylalkyl, or —($CH_2$)$_m$—A—($CH_2$)$_n$—Q;

m is 1 to 6 and n is 0 to 6;

A is —O—, —S—, —NR C═O, or a single bond;

Q is phenyl substituted with $R^7$ or naphthyl substituted with $R^7$;

$R^7$ is hydrogen, $C_1$–$C_6$ alkyl, $C_1$–$C_6$ alkoxy, hydroxy, halogen, amino, di($C_1$–$C_6$ alkyl)amino, nitro, $C_1$–$C_6$ thioalkoxy, aryl, heteroaryl, aryloxy, —CO-aryl, or arylthio;

$R^4$ and $R^5$ are each independently hydrogen, $C_1$–$C_6$ alkyl or —$NR^4R^5$ represents a 5-, 6- or 7-membered ring containing nitrogen; and $R^6$ is hydrogen, $C_1$–$C_6$ alkyl, $C_1$–$C_6$ alkoxy, hydroxy, halogen, amino, di($C_1$–$C_6$ alkyl)amino, nitro, or $C_1$–$C_6$ thioalkoxy, and one or more atoms in the compound has been replaced with a radioisotope.

DETAILED DESCRIPTION OF THE INVENTION

This invention provides a method of imaging amyloid deposits that comprises introducing into a tissue or a patient a detectable quantity of a labeled compound of Formula I or a pharmaceutically acceptable salt, ester, amide, or prodrug thereof

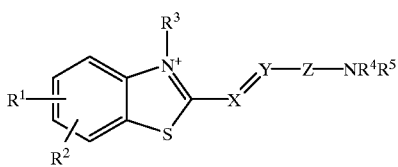

wherein

X and Y are each independently C or N and the X=Y double bond has the trans configuration;

Z is

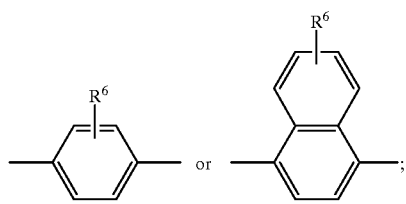

$R^1$ and $R^2$ are each independently hydrogen, $C_1$–$C_6$ alkyl, $C_1$–$C_6$ alkoxy, hydroxy, halogen, amino, mono($C_1$–$C_6$ alkyl)amino, di($C_1$–$C_6$ alkyl)amino, nitro, $C_1$–$C_6$ thioalkoxy, or $R^1$ and $R^2$ combined form a benzene, cyclopentane, or cyclohexane ring that is fused to the phenyl ring;

$R^3$ is a lone pair of electrons, $C_1$–$C_{10}$ alkyl, $C_2$–$C_{10}$ alkenyl, arylalkyl, (heteroaryl)alkyl, (cycloalkyl)alkyl, arylalkenyl, diarylalkyl or —$(CH_2)_m$—A—$(CH_2)_n$—Q;

m is 1 to 6 and n is 0 to 6;

A is —O—, —S—, —$NR^{4}$—, C=O, or a single bond;

Q is phenyl substituted with $R^7$ or naphthyl substituted with $R^7$;

$R^7$ is hydrogen, $C_1$–$C_6$ alkyl, $C_1$–$C_6$ alkoxy, hydroxy, halogen, amino, di($C_1$–$C_6$ alkyl)amino, nitro, $C_1$–$C_6$ thioalkoxy, aryl, heteroaryl, aryloxy, —CO-aryl, or arylthio;

$R^4$ and $R^5$ are each independently hydrogen, $C_1$–$C_6$ alkyl or —$NR^4R^5$ represents a 5-, 6- or 7-membered ring containing nitrogen; and $R^6$ is hydrogen, $C_1$–$C_6$ alkyl, $C_1$–$C_6$ alkoxy, hydroxy, halogen, amino, di($C_1$–$C_6$ alkyl)amino, nitro, or $C_1$–$C_6$ thioalkoxy;

allowing sufficient time for the labeled compound to become associated with amyloid deposits; and detecting the labeled compound associated with the amyloid deposits.

In a preferred embodiment of the invention,

X=Y is C=C or N=N;

$R^1$ and $R^2$ are each independently hydrogen, $C_1$–$C_6$ alkyl, $C_1$–$C_6$ alkoxy, halogen, nitro, $C_1$–$C_6$ thioalkoxy, or $R^1$ and $R^2$ combined form a benzene, cyclopentane or cyclohexane ring that is fused to the phenyl ring;

$R^3$ is $C_1$–$C_{10}$ alkyl, $C_2$–$C_{10}$ alkenyl, arylalkyl, (cycloalkyl)alkyl, arylalkenyl, diarylalkyl, or —$(CH_2)_m$—A—$(CH_2)_n$—Q;

m is 1 to 5 and n is 0 to 4;

A is —O—, —S—, or a single bond;

Q is phenyl substituted with $R^7$ or naphthyl substituted with $R^7$;

$R^7$ is hydrogen, $C_1$–$C_6$ alkyl, $C_1$–$C_6$ alkoxy, hydroxy, halogen, amino, di($C_1$–$C_6$ alkyl)amino, nitro, $C_1$–$C_6$ thioalkoxy, aryl, aryloxy, —CO-aryl, or arylthio;

$R^4$ and $R^5$ are each independently hydrogen or $C_1$–$C_6$ alkyl; and $R^6$ is hydrogen, $C_1$–$C_6$ alkyl, or halogen.

In a more preferred embodiment of the invention,

X=Y is C=C or N=N;

$R^1$ and $R^2$ are each independently hydrogen, $C_1$–$C_6$ alkyl, $C_1$–$C_6$ alkoxy, halogen, nitro, or $R^1$ and $R^2$ combined form a (4,5), (5,6), or (6,7) benzene ring that is fused to the phenyl ring;

R is $C_1$–$C_{10}$ alkyl, $C_2$–$C_{10}$ alkenyl, arylalkyl, arylalkenyl, diarylalkyl, or —$(CH_2)_m$—A—$(CH_2)_n$—Q;

m is 2 to 4 and n is 0 to 3;

A is —O—, or a single bond;

Q is phenyl substituted with $R^7$ or naphthyl substituted with $R^7$;

$R^7$ is hydrogen, $C_1$–$C_6$ alkyl, $C_1$–$C_6$ alkoxy, hydroxy, halogen, aryl, aryloxy, or —CO-aryl;

$R^4$ and $R^5$ are each independently hydrogen, methyl, ethyl, n-propyl or n-butyl; and $R^6$ is hydrogen or halogen.

In a most preferred embodiment of the invention, the labeled compound is (E)-{4-[2-(5-Chlorobenzothiazol-2-yl)vinyl]phenyl}dimethylamine;

(E)-{4-[2-Benzothiazol-2-yl)vinyl])phenyl}dimethylamine;

(E)-Dimethyl-{4-[2-(5-methylbenzothiazol-2-yl)vinyl]phenyl}amine;

(E)-Dimethyl-{4-[2-(6-methylbenzothiazol-2-yl)vinyl]phenyl}amine;

(E)-{2-[2-(4-Dimethylaminophenyl)vinyl]benzothiazol-6-yl}dimethylamine;

(E)-3-Benzyl-2-[2-(4-dimethylaminophenyl)vinyl]benzothiazol-3-ium bromide;

(E)-2-[2-(4-Dimethylaminophenyl)vinyl]-3-ethylbenzothiazol-3-ium iodide;

(E)-2-[2-(4-Dimethylaminophenyl)vinyl]-1-methylnaphtho[1,2-d]thiazol-3-ium iodide;

(E)-2-[2-(4-Dimethylaminophenyl)vinyl]-3-methylbenzothiazol-3-ium iodide;

(E)-2-[2-(4-Dimethylaminophenyl)vinyl]-3-allylbenzothiazol-3-ium bromide;

(E)-2-[2-(4-Dimethylaminophenyl)vinyl]-3-butylbenzothiazol-3-ium iodide;

(E)-2-[2-(4-Dimethylaminophenyl)vinyl]-3-heptylbenzothiazol-3-ium iodide;

(E)-5-Chloro-2-[2-(4-dimethylaminophenyl)vinyl]-3-methylbenzothiazol-3-ium iodide;

(E)-2-[2-(4-Dimethylaminophenyl)vinyl]-5-fluoro-3-methylbenzothiazol-3-ium iodide;

(E)-2-[2-(4-Dimethylaminophenyl)vinyl]-3-benzyl-5-fluorobenzothiazol-3-ium bromide;

(E)-2-[2-(4-Dimethylaminophenyl)vinyl]-3,5-dimethylbenzothiazol-3-ium iodide;

(E)-2-[2-(4-Dimethylaminophenyl)vinyl]-3,6-dimethylbenzothiazol-3-ium iodide;

(E)-3-Benzyl-2-[2-(4-dimethylaminophenyl)vinyl]-6-methylbenzothiazol-3-ium bromide;

(E)-2-[2-(4-Dimethylaminophenyl)vinyl]-6-methoxy-3-methylbenzothiazol-3-ium iodide;

(E)-2-[2-(4-Dimethylaminophenyl)vinyl]-3-heptyl-6-methoxybenzothiazol-3-ium iodide;

(E)-2-[2-(4-Dimethylaminophenyl)vinyl]-3-methyl-6-nitrobenzothiazol-3-ium toluene-4-sulfonate;

(E)-2-[2-(4-Dimethylaminophenyl)vinyl]-1-ethylnaphtho[1,2-d]thiazol-1-ium toluene-4-sulfonate;
(E)-2-[2-(4-Dimethylaminophenyl)vinyl]-3-methylnaphtho[2,3-d]thiazol-3-ium iodide;
(E)-2-[2-(4-Dimethylaminophenyl)vinyl]-3-methylnaphtho[2,1-d]thiazol-3-ium iodide;
(E)-2-[2-(4-Dimethylaminophenyl)vinyl]-3-(4-fluorobenzyl)benzothiazol-3-ium bromide;
(E)-3-Biphenyl-4-ylmethyl-2-[2-(4-dimethylaminophenyl)vinyl]benzothiazol-3-ium iodide;
(E)-2-[2-(4-Dimethylaminophenyl)vinyl]-3-naphthalen-2-ylmethylbenzothiazol-3-ium bromide;
(E)-3-Biphenyl-2-ylmethyl-2-[2-(4-dimethylaminophenyl)vinyl]benzothiazol-3-ium bromide;
(E)-3-(3-Benzoylbenzyl)-2-[2-(4-dimethylaminophenyl)vinyl]benzothiazol-3-ium bromide;
(E)-2-[2-(4-Dimethylaminophenyl)vinyl]-3-(3-phenoxybenzyl)benzothiazol-3-ium bromide
(E)-2-[2-(4-Dimethylaminophenyl)vinyl]-3-(3-phenylpropyl)benzothiazol-3-ium iodide;
(E,E)-2-[2-(4-Dimethylaminophenyl)vinyl]-3-(3-phenylallyl)benzothiazol-3-ium bromide;
(E)-2-[2-(4-Dimethylaminophenyl)vinyl]-3-(4,4-diphenylbutyl)benzothiazol-3-ium iodide;
(E)-3-(3-Benzyloxypropyl)-2-[2-(4-dimethylaminophenyl)vinyl]benzothiazol-3-ium iodide;
(E)-2-[2-(4-Dimethylaminophenyl)vinyl]-3-(4-phenoxybutyl)benzothiazol-3-ium iodide;
(E)-2-[2-(4-Dimethylaminophenyl)vinyl]-3-(5-phenylpentyl)benzothiazol-3-ium iodide;
(E)-2-[2-(4-Dimethylaminophenyl)vinyl]-3-(5-phenoxypentyl)benzothiazol-3-ium iodide;
(E)-3-(2-Cyclohexylethyl)-2-[2-(4-dimethylaminophenyl)vinyl]benzothiazol-3-ium iodide;
(E)-2-[2-(4-Dimethylaminonaphthalen-1-yl)vinyl]-3-heptylbenzothiazol-3-ium iodide;
(E)-2-[2-(4-Dimethylaminophenyl)vinyl]-3-(2-hydroxyethyl)benzothiazol-3-ium bromide;
(E)-2-[2-(4-Dimethylaminonaphthalen-1-yl)vinyl]-6-methoxy-3-methylbenzothiazol-3-ium iodide;
(E)-2-[2-(4-Dimethylaminonaphthalen-1-yl)vinyl]-1-methylnaphtho[1,2-d]thiazol-1-ium toluene-4-sulfonate;
(E)-2-[2-(4-Diethylaminophenyl)vinyl]-3-methylbenzothiazol-3-ium chlordide;
(E)-2-[2-(4-Dibethylaminophenyl)vinyl]-3-heptylbenzothiazol-3-ium iodide;
(E)-2-[2-(4-Dibutylaminophenyl)vinyl]-3-heptylbenzothiazol-3-ium iodide;
(E)-3-Heptyl-2-[2-[(4-pyrrolidin-1-yl)phenyl]vinyl]benzothiazol-3-ium iodide;
[4-(Dimethylamino)phenylazo]benzothiazole;
4-(Benzothiazol-2-ylazo)naphthalen-1-ylamine;
2-[[4-(Dimethylamino)phenyl]azo]-6-methoxybenzothiazole;
6-Chloro-2-[[4-(dimethylamino)phenyl]azo]benzothiazole;
[4-(6-Methoxybenzothiazol-2-ylazo)naphthalen-1-yl]dimethylamine;
Dimethyl[4-(naphtho[1,2-d]thiazol-2-ylazo)naphthalen-1-yl]-amine;
2-[[(4-Dimethylamino)phenyl]azo]-6-methoxy-3-methylbenzothiazol-3-ium methylsulfate; and
2-[[(4-Dimethylamino)phenyl]azo]-3-methylbenzothiazolium methylsulfate.

It is recognized that many of the compounds above are salts. The free (nonsalt) compounds are also intended.

The term "alkyl" means a straight or branched chain hydrocarbon. Representative examples of alkyl groups are methyl, ethyl, propyl, isopropyl, isobutyl, butyl, tert-butyl, sec-butyl, pentyl, and hexyl.

The term "alkoxy" means an alkyl group attached to an oxygen atom. Representative examples of alkoxy groups include methoxy, ethoxy, tert-butoxy, propoxy, and isobutoxy.

The term "halogen" includes chlorine, fluorine, bromine, and iodine.

The term "di(alkyl)amine" means an amine group having two hydrogens replaced by alkyl groups. Representative examples of di(alkyl)amines are dimethylamine, diethylamine, and methylethylamine.

The term "alkyenyl" means a branched or straight chain hydrocarbon containing one or more carbon-carbon double bond.

The term "aryl" means an aromatic hydrocarbon. Representative examples of aryl groups include phenyl and naphthyl.

The term "arylalkyl" means an alkyl group substituted with an aryl group. Representative examples are benzyl and phenylethyl.

The term "heteroatom" includes oxygen, nitrogen, and sulfur.

The term "heteroaryl" means an aryl group wherein one or more carbon atom of the aromatic hydrocarbon has been replaced with a heteroatom.

The term "(heteroaryl)alkyl" means an alkyl group substituted with a heteroaryl group.

The term "cycloalkyl" means a cyclic hydrocarbon. Examples of cycloalkyl groups include cyclopropyl, cyclobutyl, cyclopentyl, and cyclohexyl.

The term "arylalkenyl" means an alkenyl group substituted with and aryl group.

The term "diarylalkyl" means an alkyl group substituted with two aryl groups.

The term "aryloxy" means an aryl group attached to an oxygen atom.

The term "arylthio" means an aryl group attached to a sulfur atom.

The term "thioalkoxy" means an alkyl group attached to a sulfur atom.

The symbol "—" means a covalent bond.

The term "pharmaceutically acceptable salt, ester, amide, and prodrug" as used herein refers to those carboxylate salts, amino acid addition salts, esters, amides, and prodrugs of the compounds of the present invention which are, within the scope of sound medical judgement, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively nontoxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactiobionate and laurylsulphonate salts, and the like. These may include cations based on the alkali and alkaline earth metals, such as sodium, lithium, potassium, calcium, magnesium, and the like, as well as, nontoxic ammonium, quaternary ammonium and amine cations including, but not limited to ammonium, tetramethylammonium, tetraethylammonium, methylamine, dimethylamine, trimethylamine, triethylamine, ethylamine, and the like. (See, for example, Berge S. M., et al., Pharmaceutical Salts, *J. Pharm. Sci.,* 66:1–19 (1977) which is incorporated herein by reference.)

Examples of pharmaceutically acceptable, nontoxic esters of the compounds of this invention include $C_1$–$C_6$ alkyl esters wherein the alkyl group is a straight or branched chain. Acceptable esters also include $C_5$–$C_7$ cycloalkyl esters as well as arylalkyl esters such as, but not limited to benzyl. $C_1$–$C_4$ alkyl esters are preferred. Esters of the compounds of the present invention may be prepared according to conventional methods.

Examples of pharmaceutically acceptable, nontoxic amides of the compounds of this invention include amides derived from ammonia, primary $C_1$–$C_6$ alkyl amines and secondary $C_1$–$C_6$ dialkyl amines wherein the alkyl groups are straight or branched chain. In the case of secondary amines, the amine may also be in the form of a 5- or 6-membered heterocycle containing one nitrogen atom. Amides derived from ammonia, $C_1$–$C_3$ alkyl primary amides and $C_1$–$C_2$ dialkyl secondary amides are preferred. Amides of the compounds of the invention may be prepared according to conventional methods.

The term "prodrug" refers to compounds that are rapidly transformed in vivo to yield the parent compound of the above formulas, for example, by hydrolysis in blood. A thorough discussion is provided in T. Higuchi and V. Stella, *Pro-drugs as Novel Delivery Systems,* Vol. 14 of the A.C.S. Symposium Series, and in *Bioreversible Carriers in Drug Design,* ed. Edward B. Roche, American Pharmaceutical Association and Pergamon Press, 1987, both of which are incorporated herein by reference.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The compounds of the present invention can exist in different stereoisometric forms by virtue of the presence of asymmetric centers in the compounds. It is contemplated that all stereoisometric forms of the compounds, as well as mixture thereof, including racemic mixtures, form part of this invention.

In the first step of the present method of imaging, a labeled compound of Formula I is introduced into a tissue or a patient in a detectable quantity. The compound is typically part of a pharmaceutical composition and is administered to the tissue or the patient by methods well known to those skilled in the art.

For example, the compound can be administered either orally, rectally, parenterally (intravenous, by intramuscularly or subcutaneously), intracisternally, intravaginally, intraperitoneally, intravesically, locally (powders, ointments or drops), or as a buccal or nasal spray.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents, or vehicles include water, ethanol, polyols (propyleneglycol, polyethyleneglycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates and sodium carbonate; (e) solution retarders, as for example paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft- and hard-filled gelatin capsules using such excipients as lactose or milk sugar, as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, and sesame oil, glycerol, tetrahydrofurfuryl alcohol, polyethyleneglycols, and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable nonirritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers or propellants as may be required. Ophthalmic formulations, eye ointments, powders, and solutions are also contemplated as being within the scope of this invention.

In a preferred embodiment of the invention, the labeled compound is introduced into a patient in a detectable quantity and after sufficient time has passed for the compound to become associated with amyloid deposits, the labeled compound is detected noninvasively inside the patient. In another embodiment of the invention, a labeled compound of Formula I is introduced into a patient, sufficient time is allowed for the compound to become associated with amyloid deposits, and then a sample of tissue from the patient is removed and the labeled compound in the tissue is detected apart from the patient. In a third embodiment of the invention, a tissue sample is removed from a patient and a labeled compound of Formula I is introduced into the tissue sample. After a sufficient amount of time for the compound to become bound to amyloid deposits, the compound is detected.

The administration of the labeled compound to a patient can be by a general or local administration route. For example, the labeled compound may be administered to the patient such that it is delivered throughout the body. Alternatively, the labeled compound can be administered to a specific organ or tissue of interest. For example, it is desirable to locate and quantitate amyloid deposits in the brain in order to diagnose or track the progress of Alzheimer's disease in a patient.

The term "tissue" means a part of a patient's body. Examples of tissues include the brain, heart, liver, blood vessels, and arteries. A detectable quantity is a quantity of labeled compound necessary to be detected by the detection method chosen. The amount of a labeled compound to be introduced into a patient in order to provide for detection can readily be determined by those skilled in the art. For example, increasing amounts of the labeled compound can be given to a patient until the compound is detected by the detection method of choice. A label is introduced into the compounds to provide for detection of the compounds.

The term "patient" means humans and other animals. Those skilled in the art are also familiar with determining the amount of time sufficient for a compound to become associated with amyloid deposits. The amount of time necessary can easily be determined by introducing a detectable amount of a labeled compound of Formula I into a patient and then detecting the labeled compound at various times after administration.

The term "associated" means a chemical interaction between the labeled compound and the amyloid deposit. Examples of associations include covalent bonds, ionic bonds, hydrophilic-hydrophilic interactions, hydrophobic-hydrophobic interactions, and complexes.

Those skilled in the art are familiar with the various ways to detect labeled compounds. For example, magnetic resonance imaging (MRI), positron emission tomography (PET), or single photon emission computed tomography (SPECT) can be used to detect radiolabeled compounds. The label that is introduced into the compound will depend on the detection method desired. For example, if PET is selected as a detection method, the compound must possess a positron-emitting atom, such as $^{11}C$ or $^{8}F$.

Another example of a suitable label in a compound of Formula I is an atom such as $^{13}C$, $^{15}N$, or $^{19}F$ which can be detected using magnetic resonance imaging (MRI) which is also sometimes called nuclear magnetic resonance (NMR). In addition, the labeled compounds of Formula I may also be detected by MRI using paramagnetic contrast agents.

Another example of detection is electron paramagnetic resonance (EPR). In this case, EPR probes which are well-known in the art, such as nitroxides, can be used.

The imaging of amyloid deposits can also be carried out quantitatively so that the amount of amyloid deposits can be determined.

The present invention also provides a method of delivering a therapeutic agent to an amyloid deposit comprising introducing into a patient a compound having the formula

A—B—C or a pharmaceutically acceptable salt, ester, amide or pro-drug thereof, wherein A is

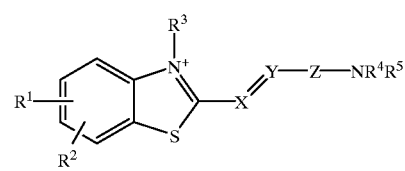

X and Y are each independently C or N and the X=Y double bond has the trans configuration;

Z is

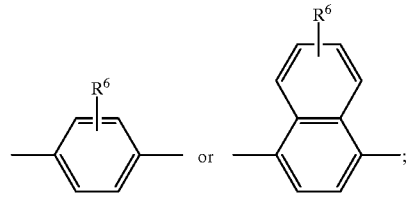

$R^1$ and $R^2$ are each independently hydrogen, $C_1$–$C_6$ alkyl, $C_1$–$C_6$ alkoxy, hydroxy, halogen, amino, di($C_1$–$C_6$ alkyl)amino, nitro, $C_1$–$C_6$ thioalkoxy or $R^1$ and $R^2$ combined form a benzene, cyclopentane, or cyclohexane ring that is fused to the phenyl ring;

$R^3$ is a lone pair of electrons, $C_1$–$C_{10}$ alkyl, $C_2$–$C_{10}$ alkenyl, arylalkyl, (heteroaryl)alkyl, (cycloalkyl)alkyl, arylalkenyl, diarylalkyl or —$(CH_2)_m$—A—$(CH_2)_n$—Q;

m is 1 to 6 and n is 0 to 6;

A is —O—, —S—, —$NR^{4-}$, C=O, or a single bond;

Q is phenyl substituted with $R^7$ or naphthyl substituted with $R^7$;

$R^7$ is hydrogen, $C_1$–$C_6$ alkyl, $C_1$–$C_6$ alkoxy, hydroxy, halogen, amino, di($C_1$–$C_6$ alkyl)amino, nitro, $C_1$–$C_6$ thioalkoxy, aryl, heteroaryl, aryloxy, —CO-aryl or arylthio;

$R^4$ and $R^5$ are each independently hydrogen, $C_1$–$C_6$ alkyl or —$NR^4R^5$ represents a 5-, 6-, or 7-membered ring containing nitrogen; and $R^6$ is hydrogen, $C_1$–$C_6$ alkyl, $C_1$–$C_6$ alkoxy, hydroxy, halogen, amino, di($C_1$–$C_6$ alkyl)amino, nitro, or $C_1$–$C_6$ thioalkoxy;

B is a linking moiety or a bond; and

C is a therapeutic agent.

The linking moiety B can be any linking moiety known to those skilled in the art. The linking moiety is used to attach the therapeutic agent C to a Compound A that binds to amyloids deposits. Examples of suitable linking moieties include, but are not limited to, covalent bonds, amino acids, peptides or proteins, alkyl chains, hydroxyacids, and diacids.

The therapeutic agent C can be any therapeutic agent known to those skilled in the art. In particular, the therapeutic agent is one that is intended for delivery to amyloid deposits or to the organs containing amyloid deposits. For example, the therapeutic agent can block or inhibit the growth or toxicity of amyloid deposits. The therapeutic agents can also aid in the degradation of amyloid deposits such as through proteolytic degradation. Examples of suitable therapeutic agents include, but are not limited to, nonsteroidal anti-inflammatory compounds (NSAIDS) such as ibuprofen or indomethacin, or compounds that affect the rate of production of the amyloid proteins.

The present invention also provides a method of inhibiting the aggregation of amyloid proteins to form amyloid deposits, by administering to a patient an amyloid inhibiting amount of a compound of Formula I. Those skilled in the art are readily able to determine an amyloid inhibiting amount by simply administering a compound of Formula I to a patient in increasing amounts until the growth of amyloid deposits is decreased or stopped. The rate of growth can be assessed using imaging as described above or by taking a tissue sample from a patient and observing the amyloid deposits therein.

The present invention also provides a method for determining a compound's ability to inhibit the aggregation of amyloid proteins. The method comprises combining the compound to be tested with amyloidogenic proteins under conditions known to produce amyloid aggregates, introducing into the assay vessel solution a labeled compound of Formula I, filtering or centrifuging the solution and determining the amount of labeled compound in the filter or filtrate, or supernatant.

The compounds of Formula I bind amyloid deposits or aggregated amyloid proteins preferentially to soluble pre-amyloid proteins. Thus, if the pre-amyloid proteins in solution aggregate, compounds of Formula I will bind to the aggregates and amyloid deposits and the associated labeled compound will be retained by the filter. However, if aggregation is inhibited by the compound of interest, then the labeled compound of Formula I will not bind to the amyloid proteins and will pass through the filter.

The compounds to be tested for ability to inhibit the aggregation of amyloid proteins can be any compound in which one skilled in the art suspects have amyloid aggregation inhibiting activity or can be chosen at random from a natural product or chemical libraries. The solution can be any solution in which amyloid proteins, a compound to be tested and a compound of Formula I are soluble. Preferably, the solution is an aqueous solution. The label may be any label known to those skilled in the art that can be detected and quantitated. For example, a preferred label is a radiolabel.

Also provided by the present invention are compounds of Formula I wherein one or more atom in the compound has been replaced with a radioisotope. The radioisotope can be any radioisotope. However, $^3$H, $^{123}$I, $^{125}$I, $^{131}$I, $^{11}$C, and $^{18}$F are preferred.

The compounds of the present invention can be administered to a patient at dosage levels in the range of about 0.1 to about 1,000 mg per day. For a normal human adult having a body weight of about 70 kg, a dosage in the range of about 0.01 to about 100 mg per kilogram of body weight per day is sufficient. The specific dosage used, however, can vary. For example, the dosage can depend on a number of factors including the requirements of the patient, the severity of the condition being treated, and the pharmacological activity of the compound being used. The determination of optimum dosages for a particular patient is well known to those skilled in the art.

The examples presented below are intended to illustrate particular embodiments of the invention and are not intended to limit the scope of the specification, including the claims, in any manner.

EXAMPLES

Synthesis of Compounds of Formula I and Labeled Compounds of Formula I

Example 1

(E)-{4-[2-(5-Chlorobenzothiazol-2-yl)vinyl] phenyl}dimethylamine

The procedure of Cuadro, et al., *Il Farmaco.*, 47:477–488 (1992), was followed. A suspension of 2-methyl-5-chlorobenzothiazole (3.78 g, 20.6 mmol), 4-(dimethylamino) benzaldehyde (3.04 g, 20.4 mmol), and 0.5 g of benzyltriethylammonium chloride in 30 mL of 50% aqueous sodium hydroxide solution was mechanically stirred in an ultrasonic bath at room temperature for 12 hours. Water (20 mL) was added, the mixture was cooled, filtered, and the solid was washed with water to give the title compound as a yellow solid, mp 182–184° C.

Example 2

(E)-{4-[2-(Benzothiazol-2-yl)vinyl]phenyl}dimethylamine was purchased from the Aldrich Chemical Co.

In a process analogous to Example 1, using appropriately substituted 2-methylbenzothiazoles, the corresponding compounds were prepared as follows:

Example 3

(E)-Dimethyl-{4-[2-(5-methylbenzothiazol-2-yl)vinyl] phenyl}amine, mp 192–194° C.

Example 4

(E)-Dimethyl-{4-[2-(6-methylbenzothiazol-2-yl)vinyl] phenyl}amine, mp 219–220.5° C.

Example 5

(E)-{2-[2-(4-Dimethylaminophenyl)vinyl]benzothiazol-6-yl}dimethylamine, mp 237–240° C.

Example 6

(E)-3-Benzyl-2-[2-(4-dimethylaminophenyl)vinyl] benzothiazol-3-ium bromide
Step (a) 3-Benzyl-2-methylbenzothiazolium bromide A solution of 2-methylbenzothiazole (5.0 g, 0.033 mol) and benzyl bromide (40 mL, 0.33 mol) in 250 mL of ethyl acetate was refluxed under nitrogen for 48 hours. Solid had formed. The mixture was filtered and washed with cold ethyl acetate to give 3-benzyl-2-methylbenzothiazol-3-ium bromide as a light yellow solid, mp 230–231° C.
Step (b) (E)-2-[2-(4-Dimethylaminophenyl)vinyl]-3-benzylbenzothiazol-3-ium bromide A mixture of 3-benzyl-2-methylbenzothiazol-3-ium bromide (0.30 g, 0.94 mmol) and 4-dimethylaminobenzaldehyde (0.21 g, 1.41 mmol) in 5 mL of acetic anhydride was heated under nitrogen. Upon refluxing, the mixture turned red and all solids appeared to be in solution. The solution was refluxed for 15 minutes, cooled, and filtered. The solid was washed with ethyl acetate to give (E)-2-[2-(4-dimethylaminophenyl)vinyl]-3-benzylbenzothiazol-3-ium bromide as a purple solid, mp 247–248° C., decomposed (dec).

Example 7

(E)-2-[2-(4-Dimethylaminophenyl)vinyl]-3-ethylbenzothiazol-3-ium iodide was purchased from the Aldrich Chemical Co.

Example 8
(E)-2-[2-(4-Dimethylaminophenyl)vinyl]-1-methylnaphtho[1,2-d]thiazol-3-ium iodide was purchased from the Sigma Chemical Co.

In a process analogous to Example 2, appropriately substituted 2-methylbenzothiazoles were alkylated with various alkyl halides then condensed with 4-dimethylaminobenzaldehyde in acetic anhydride, the corresponding compounds were prepared as follows:

Example 9
(E)-2-[2-(4-Dimethylaminophenyl)vinyl]-3-methylbenzothiazol-3-ium iodide, 251–254° C., dec.

Example 10
(E)-2-[2-(4-Dimethylaminophenyl)vinyl]-3-allylbenzothiazol-3-ium bromide, 237–240° C., dec.

Example 11
(E)-2-[2-(4-Dimethylaminophenyl)vinyl]-3-butylbenzothiazol-3-ium iodide, 234–235° C., dec.

Example 12
(E)-2-[2-(4-Dimethylaminophenyl)vinyl]-3-heptylbenzothiazol-3-ium iodide, 228–229° C., dec.

Example 13
(E)-5-Chloro-2-[2-(4-dimethylaminophenyl)vinyl]-3-methylbenzothiazol-3-ium iodide, 260–261° C., dec.

Example 14
(E)-2-[2-(4-Dimethylaminophenyl)vinyl]-5-fluoro-3-methylbenzothiazol-3-ium iodide, 250–251° C.

Example 15
(E)-2-[2-(4-Dimethylaminophenyl)vinyl]-3-benzyl-5-fluorobenzothiazol-3-ium bromide, 243–245° C.

Example 16
(E)-2-[2-(4-Dimethylaminophenylvinyl]-3,5-dimethylbenzothiazol-3-ium iodide, 248–250° C., dec.

Example 17
(E)-2-[2-(4-Dimethylaminophenylvinyl]-3,6-dimethylbenzothiazol-3-ium iodide, >240° C., dec.

Example 18
(E)-3-Benzyl-2-[2-(4-dimethylaminophenyl)vinyl]-6-methylbenzothiazol-3-ium bromide, 245–247° C., dec.

Example 19
(E)-2-[2-(4-Dimethylaminophenyl)vinyl]-6-methoxy-3-methylbenzothiazol-3-ium iodide, 254–260° C., dec.

Example 20
(E)-2-[2-(4-Dimethylaminophenyl)vinyl]-3-heptyl-6-methoxybenzothiazol-3-ium iodide, 207–208° C., dec.

Example 21
(E)-2-[2-(4-Dimethylaminophenyl)vinyl]-3-methyl-6-nitrobenzothiazol-3-ium toluene-4-sulfonate, 281–282° C., dec.

Example 22
(E)-2-[2-(4-Dimethylaminophenyl)vinyl]-1-ethylnaphtho[1,2-d]thiazol-3-ium toluene-4-sulfonate, >186° C., dec.

Example 23
(E)-2-[2-(4-Dimethylaminophenyl)vinyl]-3-methylnaphtho[2,3-d]thiazol-3-ium iodide, 302–303° C., dec.

Example 24
(E)-2-[2-(4-Dimethylaminophenyl)vinyl]-3-methylnaphtho[2,1-d]thiazol-3-ium iodide, 245–247° C., dec.

Example 25
(E)-2-[2-(4-Dimethylaminophenyl)vinyl]-3-(4-fluorobenzyl)benzothiazol-3-ium bromide, 254–255° C.

Example 26
(E)-3-Biphenyl-4-ylmethyl-2-[2-(4-dimethylaminophenyl)vinyl]benzothiazol-3-ium iodide, 210–213° C.

Example 27
(E)-2-[2-(4-Dimethylaminophenyl)vinyl]-3-naphthalen-2-ylmethylbenzothiazol-3-ium bromide, 233–236° C.

Example 28
(E)-3-Biphenyl-2-ylmethyl-2-[2-(4-dimethylaminophenyl)vinyl]benzothiazol-3-ium bromide, 229–230° C.

Example 29
(E)-3-(3-Benzoylbenzyl)-2-[2-(4-dimethylaminophenyl)vinyl]benzothiazol-3-ium bromide, 231–233° C.

Example 30
(E)-2-[2-(4-Dimethylaminophenylvinyl]-3-(3-phenoxybenzyl)benzothiazol-3-ium bromide, 231–232° C.

Example 31
(E)-2-[2-(4-Dimethylaminophenylvinyl]-3-(3-phenylpropyl)benzothiazol-3-ium iodide, 268–269° C.

Example 32
(E,E)-2-[2-(4-Dimethylaminophenyl)vinyl]-3-(3-phenylallyl)benzothiazol-3-ium bromide, 220–222° C.

Example 33
(E)-2-[2-(4-Dimethylaminophenyl)vinyl]-3-(4,4-diphenylbutyl)benzothiazol-3-ium iodide, 187–189° C.

Example 34
(E)-3-(3-Benzyloxypropyl)-2-[2-(4-dimethylaminophenylvinyl]benzothiazol-3-ium iodide, 174–177° C.

Example 35
(E)-2-[2-(4-Dimethylaminophenyl)vinyl]-3-(4-phenoxybutyl)benzothiazol-3-ium iodide, 165–170° C., dec.

Example 36
(E)-2-[2-(4-Dimethylaminophenyl)vinyl]-3-(5-phenylpentyl)benzothiazol-3-ium iodide, 214–217° C.

Example 37
(E)-2-[2-(4-Dimethylaminophenyl)vinyl]-3-(5-phenoxypentyl)benzothiazol-3-ium iodide, 156–158.5° C.

Example 38
(E)-3-(2-Cyclohexylethyl)-2-[2-(4-dimethylaminophenyl)vinyl]benzothiazol-3-ium iodide, 262–264° C.

Example 39
(E)-2-[2-(4-Dimethylaminonaphthalen-1-yl)vinyl]-3-heptylbenzothiazol-3-ium iodide Step (a) 3-Heptyl-2-methylbenzothiazolium iodide A solution of 2-methylbenzothiazole (10.0 g, 0.067 mol) and 1-iodoheptane (110 mL, 0.67 mol) in 100 mL of acetronitrile was refluxed under nitrogen for 48 hours. The mixture was cooled, filtered, and the solid formed was washed with diethyl ether and recrystallized from ethanol-ethyl acetate to give 3-heptyl-2-methylbenzothiazolium iodide as a light purple solid, mp 110–113° C.

Step (b) (E)-2-[2-(4-Dimethylaminonaphthalen-1-yl)vinyl]-3-heptylbenzothiazol-3-ium iodide A mixture of 3-heptyl-2-methylbenzothiazolium iodide (0.50 g, 1.33 mmol) and 4-dimethylamino-1- naphthaldehyde (0.40 g, 2.01 mmol) in 5 mL of acetic anhydride under nitrogen was heated. Upon refluxing, the mixture turned purple and all solids seemed to be in solution. The solution was refluxed for 15 minutes and on cooling, solid formed. The mixture was filtered and washed with ethyl acetate to give (E)-2-[2-(4-dimethylaminonaphthalen-1-yl)vinyl]-3-heptylbenzothiazol-3-ium iodide as a dark brown solid, mp 195–197° C.

Example 40
(E)-2-[2-(4-Dimethylaminophenyl)vinyl]-3-(2-hydroxyethyl)benzothiazol-3-ium bromide was purchased from the Eastman Kodak Co.

In a process analogous to Example 3, using appropriately substituted 2-methylbenzothiazoles, alkyl halides, and benzaldehydes, the corresponding compounds were prepared as follows:

Example 41
(E)-2-[2-(4-Dimethylaminonaphthalen-1-yl)vinyl]-6-methoxy-3-methylbenzothiazol-3-ium iodide, 246–247° C., dec.

Example 42
(E)-2-[2-(4-Dimethylaminonaphthalen-1-yl)vinyl]-1-1-methylnaphtho[1,2-d]thiazol-1-ium toluene-4-sulfonate, 200–210° C.

Example 43
(E)-2-[2-(4-Dimethylaminophenyl)vinyl]-3-methylbenzothiazol-3-ium chloride, 188–190° C., dec.

Example 44
(E)-2-[2-(4-Diethylaminophenyl)vinyl]-3-heptylbenzothiazol-3-ium iodide, 201–202° C., dec.

Example 45
(E)-2-[2-(4-Dibutylaminophenyl)vinyl]-3-heptylbenzothiazol-3-ium iodide, 163–164° C.

Example 46
(E)-3-Heptyl-2-[2-[(4-pyrrolidin-1-yl)phenyl]vinyl] benzothiazol-3-ium iodide, 227–229° C., dec.

Example 47
[4-(Dimethylamino)phenylazo]benzothiazole

An ice-cold solution of sodium nitrite (1.65 g, 23.9 mmol) in water (15 mL) was added slowly (via syringe) to a stirring mixture at 0° C. of 2-aminobenzothiazole (3.78 g, 25.2 mmol) in water (50 mL) and concentrated sulfuric acid (7.0 mL, 126.7 mmol). During addition, the temperature was kept below 5° C. The resultant orange mixture was stirred at 0° C. for 15 minutes, then N,N-dimethylaniline was added dropwise causing the mixture to turn dark brown-black. The mixture was stirred at 0° C. for 15 minutes, an aqueous solution of sodium acetate (4.32 g in 20 mL of water) was added dropwise, stirred for 1 hour, basified with 25% sodium hydroxide solution to a pH ~12 and allowed to warm to room temperature. The mixture was filtered, the solid was washed with cold water, recrystallized from methanol, then chromatographed (silica gel, 2% methanol in methylene chloride) to give the title compound as a green solid, mp 243–246° C.

In a process analogous to Example 4, using appropriately substituted 2-aminobenzothiazoles and arylamines, the corresponding compounds were prepared as follows:

Example 48
4-(Benzothiazol-2-ylazo)naphthalen-1-ylamine

Example 49
2-[[4-(Dimethylamino)phenyl]azo]-6-methoxybenzothiazole, 213–216° C.

Example 50
6-Chloro-2-[[4-(dimethylamino)phenyl]azo]benzothiazole, 214–218° C.

Example 51
[4-(6-Methoxybenzothiazol-2-ylazo)naphthalen-1-yl] dimethylamine, 185–185° C.

Example 52
Dimethyl[4-(naphtho[1,2-d]thiazol-2-ylazo)naphthalen-1-yl]amine, 146–148° C.

Example 53
2-[[4-(Dimethylamino)phenyl]azo]-6-methoxy-3-methylbenzothiazol-3-ium methylsulfate A solution of [4-(6-methoxy-benzothiazol-2-ylazo) phenyl]-dimethyl-amine (Example 4b, 0.75 g, 2.40 mmol) and dimethyl sulfate (0.50 mL, 5.28 mmol) in 15 mL of chlorobenzene was heated under nitrogen at 70° C. for 3 hours. The solution was cooled and solid formed. The mixture was filtered, the solid was washed with diethyl ether and recrystallized from ethanol to give the title compound as a dark blue-black solid, mp 206–207° C., dec.

Example 54
2-[[4-(Dimethylamino)phenyl]azo]-3-methylbenzothiazolium methylsulfate was purchased from the Tennessee Eastman Co.

Tritiation of Example 12

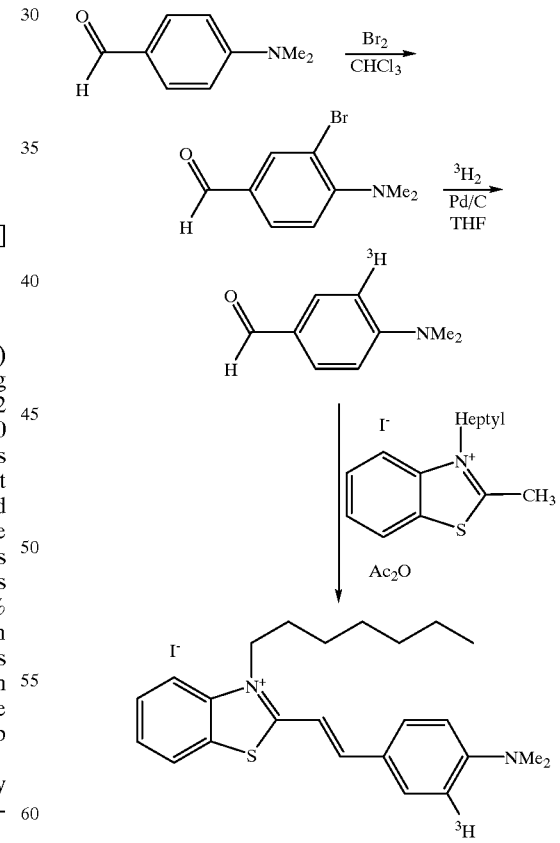

2-Bromo-4-(dimethylamino)benzaldehyde

To a solution of 4-(dimethylamino)benzaldehyde (5.0 g, 33.5 mmol) in chloroform (30 mL) was added benzoyl peroxide (10 mg). Bromine (5.43 g, 34 mmol) in chloroform (10 mL) was added dropwise to the solution of aldehyde over a 30 minute period. The reaction was stirred an additional hour, and the chloroform solution was washed with 5% NaHCO$_3$, dried (MgSO$_4$), and concentrated. The crude oil was chromatographed on a silica gel column eluted with methylene chloride to yield the product as a pale yellow oil (5.21 g, 68% yield).

Analysis calculated for C$_9$H$_{10}$BrNO: C, 47.39; H, 4.42; N, 6.14. Found: C, 47.08; H, 4.38; N, 6.13.

Tritiation of 2-bromo-4-(dimethylamino)benzaldehyde

To a solution of the 2-bromo-4-(dimethylamino) benzaldehyde (0.02 g) in anhydrous tetrahydrofuran was added 10% Pd/C (12 mg). The reaction was stirred under an atmosphere of tritium gas for 18 hours. The gas was removed using a gas manifold at −78° C., and the reaction was filtered through a Celite pad and concentrated. Methanol was added (3×20 mL), and the reaction was reconcentrated to remove any exchangeable tritium. The oil was partitioned between methylene chloride and 5% NaHCO$_3$. The methylene chloride layer was dried (MgSO$_4$), filtered, and concentrated. The crude product was chromatographed on a silica gel column eluted with methylene chloride. The unreacted starting material came off first followed by the tritiated 4-(dimethylamino)benzaldehyde. The product was used without additional purification or characterization.

[$^3$H]-(E)-2-[2-(4-Dimethylaminophenyl)vinyl]-3-heptylbenzothiazol-3-ium iodide The procedure used to prepare Example 44 was applied to the reaction of [$^3$H]-4-(dimethylamino)benzaldehyde with 3-heptyl-2-methylbenzothiazolium iodide to give the title compounds specific activity 20.54 Ci/mmol.

Example of $^{131}$I-Labeling

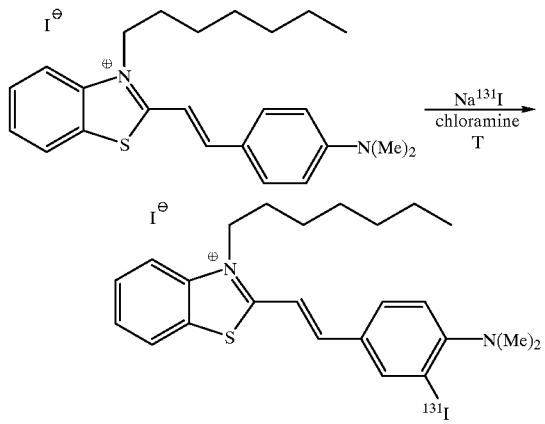

Example of $^{11}$C-Labeling

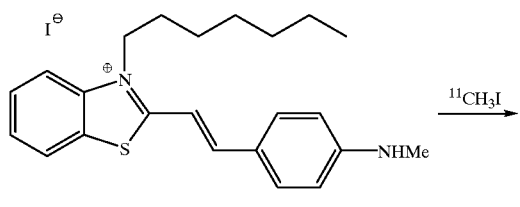

Example of $^{18}$F-Labeling

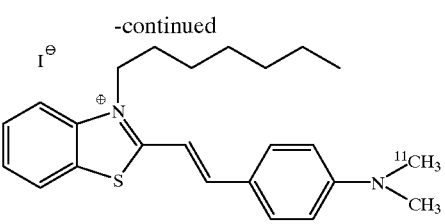

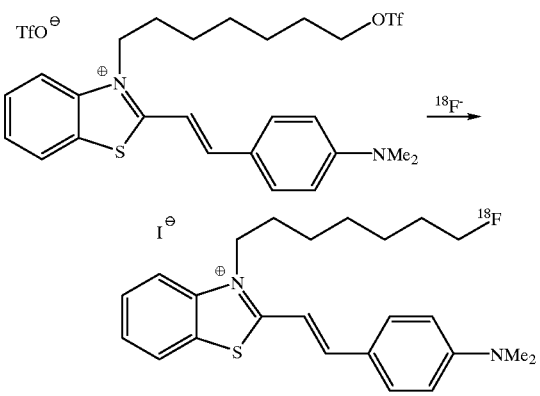

Generic Synthetic Schemes

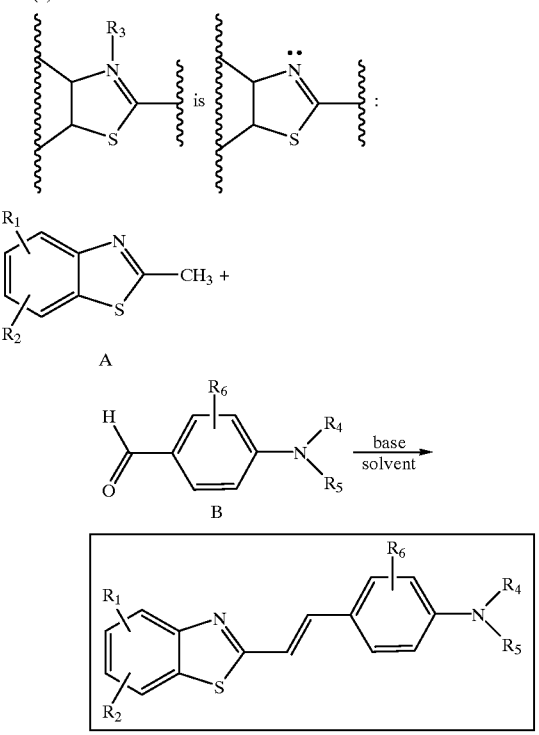

A and B are known in the art or can be prepared by known methods.

The preferred solvent is water or other polar solvents (methanol, H$_2$O/methanol mixtures, etc.);

"Base" can be NaOH, KOH, LiOH, etc., in the presence of a phase-transfer catalyst, such as PhCHeNEt₃Cl and other tetraalkylammonium halides.

(2) When X=Y is C=C and R₃ is anything other than a lone pair of electrons:

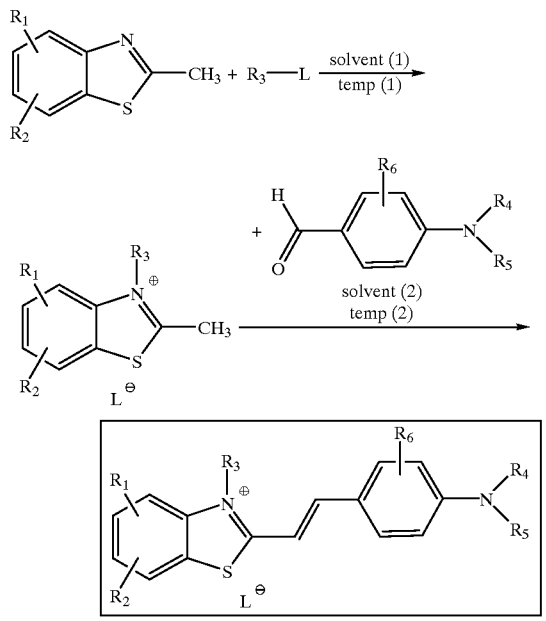

Where L is a leaving group (Br, Cl, p-toulene sulfonate (TSO), etc.);

Where solvent (1) can be any solvent that the compounds are soluble in, such as ethyl acetate, acetonitrile, ethanol, isopropanol, etc. A preferred solvent (such as ethyl acetate) is one where intermediate A crystallizes as it is formed;

Temp (1): room temperature→reflux. Preferred temperature range 40–90° C.;

Solvent (2): one in which A is soluble in and which is dehydrating, such as acetic anhydride;

Temp (2): Typically, the boiling point of solvent (2). Preferred temperature range 80–120° C.

(3) When X=Y is N=N, and

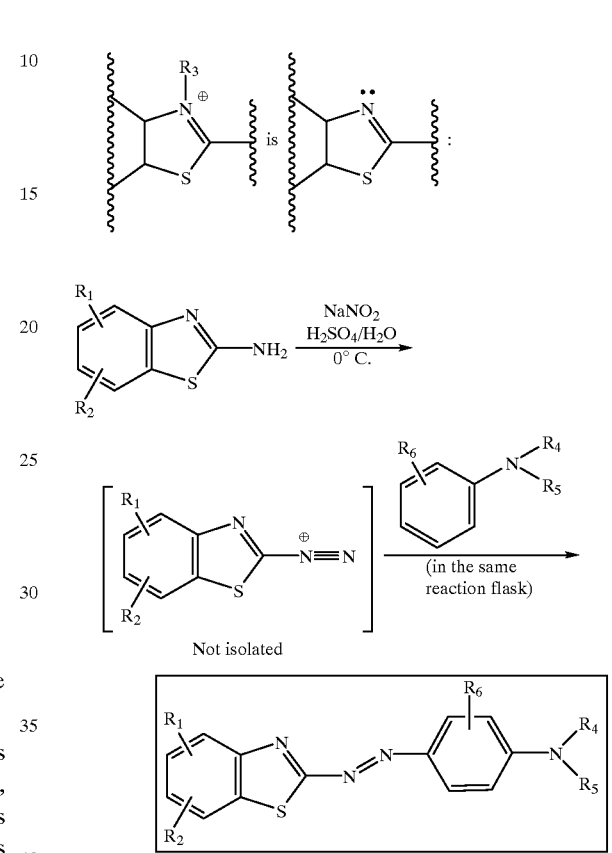

(4) When X=Y is N=N, and R₃ is anything other than a lone pair of electrons:

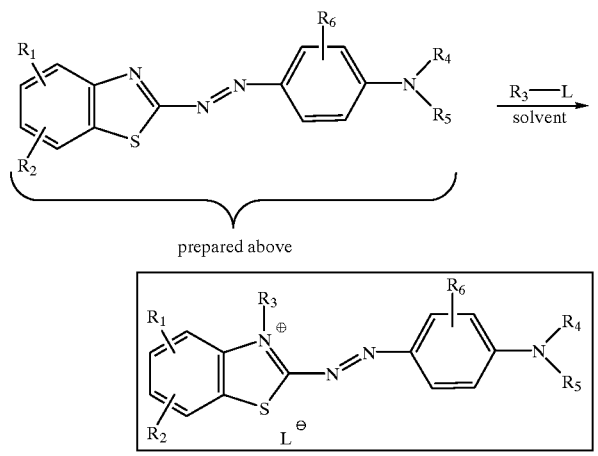

Where L is a leaving group (Cl, Br, TSO, mesylate(MSO), etc.);

Solvent can be any inert solvent, preferably one in which the product crystallizes as it is formed: chlorobenzene, toluene, etc.;

Preferred temperature range 50–100° C.

Synthesis of Amyloid Aggregates

Amyloid aggregates were prepared according to methods that are well known to those skilled in the art, and the presence of amyloid fibrin aggregates was verified by Congo Red birefringence, a method that is also well known to those skilled in the art.

Insulin Amyloid Aggregates

Burke M. J. and Rougevie M. A., Cross-β Protein Structures. I. Insulin Fibrils. *Biochemistry*, 11:2435–243 (1972), which is hereby incorporated by reference, is an example that shows how to make amyloid aggregates having insulin as a component. Briefly, lyophilized insulin protein powder dissolved at 10 mg/mL in 50 mM HCl was alternately heated to 95° C. and frozen in dry ice to form amyloid aggregates.

β(1-40) Amyloid Aggregates

Amyloid aggregates containing β(1-40) protein can also be made by methods well known to those skilled in the art. See, for example, Burdick D., Soreghan B., Kwon M., Kosmoski J., Knauer M., Henschen A., Yates J., Cotman C., and Glabe C. Assembly and aggregation properties of synthetic Alzheimer's A4/β amyloid peptide analogs. *J. Biol. Chem.*, 267:546–554 (1992), which is hereby incorporated by reference. Briefly, lyophilized β(1-40) protein powder (which may be purchased from BACHEM) was dissolved at 10 mg/mL in hexafluoro-2-propanol and subsequently diluted to 500 μg/mL in 25 mM sodium phosphate buffer, pH 6 to induce the α-helix to β-sheet transition resulting in aggregate formation.

Competition Assay

The ability of compounds of Formula I to compete with Thioflavin T (ThT) for binding to amyloid aggregates was measured using fluorescence in a 96-well fluorescence plate assay. As a compromise between sensitivity and signal and to facilitate comparisons between different amyloid fibrils, ThT is present at a concentration equal to the $K_{mapp}$ of the particular amyloid fibril type and fibril concentrations yielding a similar fluorescence intensity are used. Insulin: 0.5 μM ThT, 2 μg per well. β(1-40): 20 μM ThT, 5 μg/well. All solutions are in 25 mM sodium phosphate buffer, pH 6.0, and the assay is performed at room temperature.

Using a multichannel pipettor, 100 μL of dilutions of the compound to be tested (0.001–30 μM final concentration in 3-fold steps) are placed in the bottom of Corning U-well polystyrene plates (Corning Company, Corning, N.Y.). 50 μL of ThT are then added to each well. The amyloid fibrils are then added to each well in a volume of 100 μL rapidly to mix the well contents. The plates are read within 5 to 30 minutes in a Millipore Cytofluor 2350 96-well fluorescence plate reader using an excitation filter of 440 nm (20 nm bandpass) and an emission filter of 485 nm (20 nm bandpass). ThT dye blanks were used to correct for the minimal fluorescence background which are subtracted from all data. Amyloid fibrils do not contribute significantly to the observed signal. Settling of amyloid fibrils does not effect the observed fluorescence as the instrument reads through the bottom of the sample wells.

Results are expressed as % maximal fluorescence (no competing compound). $IC_{50}$s are defined as the concentration of compound required to reduce ThT fluorescence to 50% of its initial intensity and are estimated by log-logit analysis. The data is shown below in Table 1.

TABLE 1

| Example Number | Name | βA(1–40), $IC_{50}$ (nM) | Insulin, $IC_{50}$ (nM) |
|---|---|---|---|
| 1 | (E)-{4-[2-(5-Chlorobenzo-thiazol-2-yl)vinyl]-phenyl}dimethylamine | >100,000 | 100,000 |
| 2 | (E)-{4-[2-Benzothiazol-2-yl)vinyl])phenyl}-dimethylamine | >100,000 (F) | 1,200 |
| 3 | (E)-Dimethyl-{4-[2-(5-methylbenzothiazol-2-yl)-vinyl]phenyl}amine | (F) | 900 (F) |
| 4 | (E)-Dimethyl-{4-[2-(6-methylbenzothiazol-2-yl)-vinyl]phenyl}amine | (F) | 1,500 (F) |
| 5 | (E)-{2-[2-(4-Dimethylamino-phenyl)vinyl]benzothiazol-6-yl}dimethylamine | >100,000 | 6,000 |
| 6 | (E)-3-Benzyl-2-[2-(4-dimethylaminophenyl)-vinyl]benzothiazol-3-ium bromide | 110 | 12 |
| 7 | (E)-2-[2-(4-Dimethylamino-phenyl)vinyl]-3-ethylbenzo-thiazol-3-ium iodide | 400 | 6 |
| 8 | (E)-2-[2-(4-Dimethylamino-phenyl)vinyl]-1-methylnaphtho[1,2-d]-thiazol-3-ium iodide | 210 | 53 |
| 9 | (E)-2-[2-(4-Dimethyl-aminophenyl)vinyl[-3-methylbenzothiazol-3-ium iodide | 1,000 | 3 |
| 10 | (E)-2-[2-(4-Dimethyl-aminophenyl)vinyl[-3-allylbenzothiazol-3-ium bromide | 300 | 12 |
| 11 | (E)-2-[2-(4-Dimethyl-aminophenyl)vinyl]-3-butylbenzothiazol-3-ium iodide | 160 | 27 |
| 12 | (E)-2-[2-(4-Dimethyl-aminophenyl)vinyl]-3-heptylbenzothiazol-3-ium iodide | 93 | 83 |
| 13 | (E)-5-Chloro-2-[2-(4-dimethylaminophenyl)-vinyl]-3-methylbenzo-thiazol-3-ium iodide | 430 | 5.2 |
| 14 | (E)-2-[2-(4-Dimethyl-aminophenyl)vinyl]-5-fluoro-3-methylbenzo-thiazol-3-ium iodide | 1,000 | 10 |
| 15 | (E)-2-[2-(4-Dimethyl-aminophenyl)vinyl]-3-benzyl-5-fluorobenzo-thiazol-3-ium bromide | 170 | 32 |
| 16 | (E)-2-[2-(4-Dimethyl-aminophenyl)vinyl]-3,5-dimethylbenzothiazol-3-ium iodide | 400 | 7.5 |
| 17 | (E)-2-[2-(4-Dimethyl-aminophenyl)vinyl]-3,6-dimethylbenzothiazol-3-ium iodide | 180 | 6 |
| 18 | (E)-3-Benzyl-2-[2-(4-dimethylaminophenyl)-vinyl]-6-methylbenzo-thiazol-3-ium bromide | 130 | 50 |
| 19 | (E)-2-[2-(4-Dimethyl-aminophenyl)vinyl]-6-methoxy-3-methylbenzo-thiazol-3-ium iodide | 300 | 8 |
| 20 | (E)-2-[2-(4-Dimethyl-aminophenyl)vinyl]-3-heptyl-6-methoxybenzo-thiazol-3-ium iodide | 140 | 40 |
| 21 | (E)-2-[2-(4-Dimethyl-aminophenyl)vinyl]-3- | 1,000 | 12 |

TABLE 1-continued

| Example Number | Name | βA(1–40), IC$_{50}$ (nM) | Insulin, IC$_{50}$ (nM) |
|---|---|---|---|
|  | methyl-6-nitrobenzo-thiazol-3-ium toluene-4-sulfonate |  |  |
| 22 | (E)-2-[2-(4-Dimethyl-aminophenyl)vinyl]-1-ethylnaphtho[1,2-d]-thiazol-1-ium toluene-4-sulfonate | 210 | 41 |
| 23 | (E)-2-[2-(4-Dimethyl-aminophenyl)vinyl]-3-methylnaphtho[2,3-d]-thiazol-3-ium iodide | 120 | 120 |
| 24 | (E)-2-[2-(4-Dimethyl-aminophenyl)vinyl]-3-methylnaphtho[2,1-d]-thiazol-3-ium iodide | 210 | 41 |
| 25 | (E)-2-[2-(4-Dimethyl-aminophenyl)vinyl]-3-(4-fluorobenzyl)benzothiazol-3-ium bromide | 120 | 42 |
| 26 | (E)-3-Biphenyl-4-ylmethyl-2-[2-(4-dimethylamino-phenyl)vinyl]benzothiazol-3-ium iodide | 240 | 34 |
| 27 | (E)-2-[2-(4-Dimethyl-aminophenyl)vinyl]-3-naphthalen-2-ylmethyl-benzothiazol-3-ium bromide | 120 | 13 |
| 28 | (E)-3-Biphenyl-2-ylmethyl-2-[2-(4-dimethylamino-phenyl)vinyl]benzothiazol-3-ium bromide | 100 | 80 |
| 29 | (E)-3-(3-Benzoylbenzyl)-2-[2-(4-dimethylaminophenyl)-vinyl]benzothiazol-3-ium bromide | 230 | 130 |
| 30 | (E)-2-[2-(4-Dimethylamino-phenyl)vinyl]-3-(3-phenoxybenzyl)benzothiazol-3-ium bromide | 120 | 180 |
| 31 | (E)-2-[2-(4-Dimethyl-aminophenyl)vinyl]-3-(3-phenylpropyl)benzothiazol-3-ium iodide | 200 | 210 |
| 32 | (E-E)-2-[2-(4-Dimethyl-aminophenyl)vinyl]-3-(3-phenylallyl)benzothiazol-3-ium bromide | 100 | 80 |
| 33 | (E)-2-[2-(4-Dimethyl-aminophenyl)vinyl]-3-(4,4-diphenylbutyl)benzothiazol-3-ium iodide | 460 | 210 |
| 34 | (E)-3-(3-Benzyloxypropyl)-2-[2-(4-dimethylamino-phenyl)vinyl]benzothiazol-3-ium iodide | 140 | 52 |
| 35 | (E)-2-[2-(4-Dimethyl-aminophenyl)vinyl]-3-(4-phenoxybutyl)benzothiazol-3-ium iodide | 170 | 62 |
| 36 | (E)-2-[2-(4-Dimethyl-aminophenyl)vinyl]-3-(5-phenylpentyl)benzothiazol-3-ium iodide | 170 | 93 |
| 37 | (E)-2-[2-(4-Dimethyl-aminophenyl)vinyl]-3-(5-phenoxypentyl)benzothiazol-3-ium iodide | 170 | 80 |
| 38 | (E)-3-(2-Cyclohexylethyl)-2-[2-(4-dimethylamino-phenyl)vinyl]benzothiazol-3-ium iodide | 120 | 52 |
| 39 | (E)-2-[2-(4-Dimethyl-aminonaphthalen-1-yl)-vinyl]-3-heptylbenzo-thiazol-3-ium iodide | 160 | 40 |
| 41 | (E)-2-[2-(4-Dimethyl-aminonaphthalen-1-yl)-vinyl]-6-methoxy-3-methylbenzothiazol-3-ium iodide | 430 | 26 |
| 42 | (E)-2-[2-(4-Dimethylamino-naphthalen-1-yl)vinyl]-1-methylnaphtho[1,2-d]-thiazol-1-ium toluene-4-sulfonate | 250 | 42 |
| 43 | (E)-2-[2-(4-Dimethylamino-phenyl)vinyl]-3-methyl-benzothiazol-3-ium chloride |  |  |
| 44 | (E)-2-[2-(4-Diethylamino-phenyl)vinyl]-3-heptyl-benzothiazol-3-ium iodide | 140 | 120 |
| 45 | (E)-2-[2-(4-Dibutylamino-phenyl)vinyl-3-heptyl-benzothiazol-3-ium iodide | 600 | 90 |
| 46 | (E)-3-Heptyl-2-[2-[(4 pyrrolidin-1-yl)phenyl]-vinyl]benzothiazol-3-ium iodide | 160 | 42 |
| 47 | [4-(Dimethylamino)-phenylazo]benzothiazole | 22,000 | 1,200 |
| 48 | 4-(Benzothiazol-2-ylazo)-naphthalen-1-ylamine | 120 | 110 |
| 49 | 2-[[4-(Dimethylamino)-phenyl]azo]-6-methoxy-benzothiazole | 3,200 | 700 |
| 50 | 6-Chloro-2-[[4-(dimethyl-amino)phenyl]azo]benzo-thiazole | 1,300 | 1,300 |
| 51 | [4-(6-Methoxybenzothiazol-2-ylazo)naphthalen-1-yl]-dimethylamine | 2,500 | 340 |
| 52 | Dimethyl[4-(naphtho[1,2-d]-thiazol-2-ylazo)naphthalen-1-yl]-amine | 52,000 | 16,000 |
| 53 | 2-[[(4-Dimethylamino-phenyl]azo)-6-methoxy-3-methylbenzothiazol-3-ium methylsulfate | 410 | 10 |
| 54 | 2-[[(4-Dimethylamino)-phenyl]azo]-3-methylbenzo-thiazolium methylsulfate | 1,300 | 60 |

(F) indicates that the test compound itself is fluorescent and interferes with the assay.

Binding of [$^3$H]-2-[2-(4-Dimethylaminophenyl)vinyl]-3-heptylbenzothiazol-3-ium iodide to Amyloid Fibrils The binding reaction is carried out at room temperature in buffer (25 mM sodium phosphate, pH 6.0+0.2 mg/mL chicken ovalbumin (which can be purchased from Sigma). 33 μL of buffer containing 30,000 cpm of [$^3$H]-2-[2-(4-Dimethylaminophenyl)vinyl]-3-heptylbenzothiazol-3-ium iodide are added to 33 μL of diluted test compound in buffer in polyallomer 1.5 mL microfuge tubes (which may be purchased from Beckman). The binding reaction is initiated with 33 μL of buffer containing 300 ng of insulin amyloid fibrils and vortexing. After 45 minutes, 1.25 mL of buffer are added to each tube, vortexed, and spun at 16,000×G in a microfuge for 10 minutes. The supernatant is removed by pasteur pipet and the whole tube is placed in a 20 mL scintillation vial for determination of tritium after the addition of Ready-Gel scintillation fluid (Beckman). Nonspecific binding of label to tubes containing no amyloid fibrils or with fibrils in the presence of excess unlabeled 2-[2-(4-dimethylaminophenyl)vinyl]-3-heptylbenzothiazol-3-ium iodide give the same values and are subtracted from the total binding to obtain specific binding.

Results are expressed as % maximal specific binding. IC$_{50}$s are defined as the concentration of compound required to reduce [$^3$H]-2-[2-(4-dimethylaminophenyl)vinyl]-3-heptyl benzothiazol-3-ium iodide binding to 50% of its initial amount and are estimated by log-logit analysis. FIGS. 1 and 2 show the results.

We claim:
1. A method of imaging amyloid deposits, the method comprising:
   a. introducing into a patient a detectable quantity of a labeled compound having the Formula I or a pharmaceutically acceptable salt, ester, or amide thereof

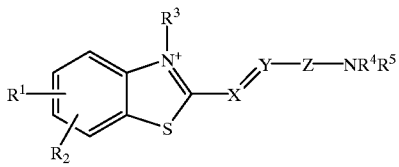

wherein
X and Y are each independently C or N and the X=Y double bond has the trans configuration;
Z is

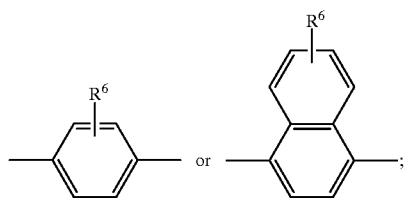

$R^1$ and $R^2$ are each independently hydrogen, $C_1$–$C_6$ alkyl, $C_1$–$C_6$ alkoxy, hydroxy, halogen, amino, di($C_1$–$C_6$ alkyl)amino, mono($C_1$–$C_6$ alkyl)amino, nitro, $C_1$–$C_6$ thioalkoxy, or $R^1$ and $R^2$ combined form a benzene, cyclopentane, or cyclohexane ring that is fused to the phenyl ring;

$R^3$ is a lone pair of electrons, $C_1$–$C_{10}$ alkyl, $C_2$–$C_{10}$ alkenyl, arylalkyl, (heteroaryl)alkyl, (cycloalkyl)alkyl, arylalkenyl, diarylalkyl or —(CH$_2$)$_m$—A—(CH 2)$_n$—Q;

m is 1 to 6 and n is 0 to 6;
A is —O—, —S—, —NR$^{4-}$, C=O, or a single bond;
Q is phenyl substituted with $R^7$ or naphthyl substituted with $R^7$;
$R^7$ is hydrogen, $C_1$–$C_6$ alkyl, $C_1$–$C_6$ alkoxy, hydroxy, halogen, amino, di($C_1$–$C_6$ alkyl)amino, nitro, $C_1$–$C_6$ thioalkoxy, aryl, heteroaryl, aryloxy, —CO-aryl, or arylthio;

$R^4$ and $R^5$ are each independently hydrogen, $C_1$–$C_6$ alkyl or —NR$^4$R$^5$ represents a 5-, 6- or 7-membered ring containing nitrogen; and $R^6$ is hydrogen, $C_1$–$C_6$ alkyl, $C_1$–$C_6$ alkoxy, hydroxy, halogen, amino, di($C_1$–$C_6$ alkyl)amino, nitro, or $C_1$–$C_6$ thioalkoxy;

b. allowing sufficient time for the labeled compound to become associated with amyloid deposits; and
c. detecting the labeled compound associated with the amyloid deposits.

2. The method of claim 1 wherein
X=Y is C=C or N=N;
$R^1$ and $R^2$ are each independently hydrogen, $C_1$–$C_6$ alkyl, $C_1$–$C_6$ alkoxy, halogen, nitro, $C_1$–$C_6$ thioalkoxy, or $R^1$ and $R^2$ combined form a benzene, cyclopentane or cyclohexane ring that is fused to the phenyl ring;

$R^3$ is $C_1$–$C_{10}$ alkyl, $C_2$–$C_{10}$ alkenyl, arylalkyl, (cycloalkyl)alkyl, arylalkenyl, diarylalkenyl, or —(CH$_2$)$_m$—A—(CH$_2$)$_n$—Q;

m is 1 to 5 and n is 0 to 4;
A is —O—, —S—, or a single bond;
Q is phenyl substituted with $R^7$ or naphthyl substituted with $R^7$;
$R^7$ is hydrogen, $C_1$–$C_6$ alkyl, $C_1$–$C_6$ alkoxy, hydroxy, halogen, amino, di($C_1$–$C_6$ alkyl)amino, nitro, $C_1$–$C_6$ thioalkoxy, aryl, aryloxy, —CO-aryl, or arylthio;

$R^4$ and $R^5$ are each independently hydrogen or $C_1$–$C_6$ alkyl; and $R^6$ is hydrogen, $C_1$–$C_6$ alkyl, or halogen.

3. The method of claim 1 wherein
X=Y is C=C or N=N;
$R^1$ and $R^2$ are each independently hydrogen, $C_1$–$C_6$ alkyl, $C_1$–$C_6$ alkoxy, halogen, nitro, or $R^1$ and $R^2$ combined form a (4,5), (5,6), or (6,7) benzene ring that is fused to the phenyl ring;

$R^3$ is $C_1$–$C_{10}$ alkyl, $C_2$–$C_{10}$ alkenyl, arylalkyl, arylalkenyl, diarylalkyl, or —(CH$_2$)$_m$—A—(CH$_2$)$_n$—Q;

m is 2 to 4 and n is 0 to 3;
A is —O—, or a single bond;
Q is phenyl substituted with $R^7$ or naphthyl substituted with $R^7$;
$R^7$ is hydrogen, $C_1$–$C_6$ alkyl, $C_1$–$C_6$ alkoxy, hydroxy, halogen, aryl, aryloxy, or —CO-aryl;

$R^4$ and $R^5$ are each independently hydrogen, methyl, ethyl, n-propyl or n-butyl; and $R^6$ is hydrogen or halogen.

4. The method of claim 1 wherein the compound is
(E)-{4-[2-(5-Chlorobenzothiazol-2-yl)vinyl]phenyl}dimethylamine;
(E)-{4-[2-Benzothiazol-2-yl)vinyl])phenyl}dimethylamine;
(E)-Dimethyl-{4-[2-(5-methylbenzothiazol-2-yl)vinyl]phenyl}amine;
(E)-Dimethyl-{4-[2-(6-methylbenzothiazol-2-yl)vinyl]phenyl}amine;
(E)-{2-[2-(4-Dimethylaminophenyl)vinyl]benzothiazol-6-yl}dimethylamine;
(E)-3-Benzyl-2-[2-(4-dimethylaminophenyl)vinyl]benzothiazol-3-ium bromide;
(E)-2-[2-(4-Dimethylaminophenyl)vinyl]-3-ethylbenzothiazol-3-ium iodide;
(E)-2-[2-(4-Dimethylaminophenyl)vinyl]-1-methylnaphtho[1,2-d]thiazol-3-ium iodide;
(E)-2-[2-(4-Dimethylaminophenyl)vinyl]-3-methylbenzothiazol-3-ium iodide;
(E)-2-[2-(4-Dimethylaminophenyl)vinyl]-3-allylbenzothiazol-3-ium bromide;
(E)-2-[2-(4-Dimethylaminophenyl)vinyl]-3-butylbenzothiazol-3-ium iodide;
(E)-2-[2-(4-Dimethylaminophenyl)vinyl]-3-heptylbenzothiazol-3-ium iodide;
(E)-5-Chloro-2-[2-(4-dimethylaminophenyl)vinyl]-3-methylbenzothiazol-3-ium iodide;
(E)-2-[2-(4-Dimethylaminophenyl)vinyl]-5-fluoro-3-methylbenzothiazol-3-ium iodide;

(E)-2-[2-(4-Dimethylaminophenyl)vinyl]-3-benzyl-5-fluorobenzothiazol-3-ium bromide;

(E)-2-[2-(4-Dimethylaminophenyl)vinyl]-3,5-dimethylbenzothiazol-3-ium iodide;

(E)-2-[2-(4-Dimethylaminophenyl)vinyl]-3,6-dimethylbenzothiazol-3-ium iodide;

(E)-3-Benzyl-2-[2-(4-dimethylaminophenyl)vinyl]-6-methylbenzothiazol-3-ium bromide;

(E)-2-[2-(4-Dimethylaminophenyl)vinyl]-6-methoxy-3-methylbenzothiazol-3-ium iodide;

(E)-2-[2-(4-Dimethylaminophenyl)vinyl]-3-heptyl-6-methoxybenzothiazol-3-ium iodide;

(E)-2-[2-(4-Dimethylaminophenyl)vinyl]-3-methyl-6-nitrobenzothiazol-3-ium toluene-4-sulfonate;

(E)-2-[2-(4-Dimethylaminophenyl)vinyl]-1-ethylnaphtho[1,2-d]thiazol-1-ium toluene-4-sulfonate;

(E)-2-[2-(4-Dimethylaminophenyl)vinyl]-3-methylnaphtho[2,3-d]thiazol-3-ium iodide;

(E)-2-[2-(4-Dimethylaminophenyl)vinyl]-3-methylnaphtho[2,1-d]thiazol-3-ium iodide;

(E)-2-[2-(4-Dimethylaminophenyl)vinyl]-3-(4-fluorobenzyl)benzothiazol-3-ium bromide;

(E)-3-Biphenyl-4-ylmethyl-2-[2-(4-dimethylaminophenyl)vinyl]benzothiazol-3-ium iodide;

(E)-2-[2-(4-Dimethylaminophenyl)vinyl]-3-naphthalen-2-ylmethylbenzothiazol-3-ium bromide;

(E)-3-Biphenyl-2-ylmethyl-2-[2-(4-dimethylaminophenyl)vinyl]benzothiazol-3-ium bromide;

(E)-3-(3-Benzoylbenzyl)-2-[2-(4-dimethylaminophenyl)vinyl]benzothiazol-3-ium bromide;

(E)-2-[2-(4-Dimethylaminophenyl)vinyl]-3-(3-phenoxybenzyl)benzothiazol-3-ium bromide (E)-2-[2-(4-Dimethylaminophenyl)vinyl]-3-(3-phenylpropyl)benzothiazol-3-ium iodide;

(E,E)-2-[2-(4-Dimethylaminophenyl)vinyl]-3-(3-phenylallyl)benzothiazol-3-ium bromide;

(E)-2-[2-(4-Dimethylaminophenyl)vinyl]-3-(4,4-diphenylbutyl)benzothiazol-3-ium iodide;

(E)-3-(3-Benzyloxypropyl)-2-[2-(4-dimethylaminophenyl)vinyl]benzothiazol-3-ium iodide;

(E)-2-[2-(4-Dimethylaminophenyl)vinyl]-3-(4-phenoxybutyl)benzothiazol-3-ium iodide;

(E)-2-[2-(4-Dimethylaminophenyl)vinyl]-3-(5-phenylpentyl)benzothiazol-3-ium iodide;

(E)-2-[2-(4-Dimethylaminophenyl)vinyl]-3-(5-phenoxypentyl)benzothiazol-3-ium iodide;

(E)-3-(2-Cyclohexylethyl)-2-[2-(4-dimethylaminophenyl)vinyl]benzothiazol-3-ium iodide;

(E)-2-[2-(4-Dimethylaminonaphthalen-1-yl)vinyl]-3-heptylbenzothiazol-3-ium iodide;

(E)-2-[2-(4-Dimethylaminophenyl)vinyl]-3-(2-hydroxyethyl)benzothiazol-3-ium bromide;

(E)-2-[2-(4-Dimethylaminonaphthalen-1-yl)vinyl]-6-methoxy-3-methylbenzothiazol-3-ium iodide;

(E)-2-[2-(4-Dimethylaminonaphthalen-1-yl)vinyl]-1-methylnaphtho[1,2-d]thiazol-1-ium toluene-4-sulfonate;

(E)-2-[2-(4-Diethylaminophenyl)vinyl]-3-methylbenzothiazol-3-ium chlordide;

(E)-2-[2-(4-Dibethylaminophenyl)vinyl]-3-heptylbenzothiazol-3-ium iodide;

(E)-2-[2-(4-Dibutylaminophenyl)vinyl]-3-heptylbenzothiazol-3-ium iodide;

(E)-3-Heptyl-2-[2-[(4-pyrrolidin-1-yl)phenyl]vinyl]benzothiazol-3-ium iodide;

[4-(Dimethylamino)phenylazo]benzothiazole;

4-(Benzothiazol-2-ylazo)naphthalen-1-ylamine;

2-[[4-(Dimethylamino)phenyl]azo]-6-methoxybenzothiazole;

6-Chloro-2-[[4-(dimethylamino)phenyl]azo]benzothiazole;

[4-(6-Methoxybenzothiazol-2-ylazo)naphthalen-1-yl]dimethylamine;

Dimethyl[4-(naphtho[1,2-d]thiazol-2-ylazo)naphthalen-1-yl]amine;

2-[[(4-Dimethylamino)phenyl]azo]-6-methoxy-3-methylbenzothiazol-3-ium methylsulfate; and 2-[[(4-Dimethylamino)phenyl]azo]-3-methylbenzothiazolium methylsulfate.

5. A method of delivering a therapeutic agent to an amyloid deposit comprising introducing into a patient a compound having the formula

A—B—C or a pharmaceutically acceptable salt, ester, or amide thereof, wherein A is

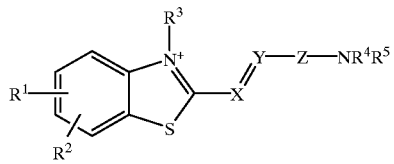

X and Y are each independently C or N and the X=Y double bond has the trans configuration;

Z is

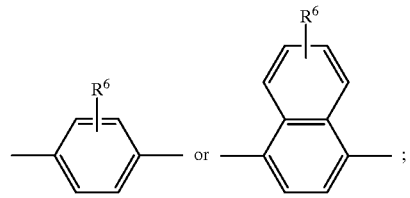

$R^1$ and $R^2$ are each independently hydrogen, $C_1-C_6$ alkyl, $C_1-C_6$ alkoxy, hydroxy, halogen, amino, di($C_1-C_6$ alkyl)amino, mono($C_1-C_6$ alkyl)amino, nitro, $C_1-C_6$ thioalkoxy or $R^1$ and $R^2$ combined form a benzene, cyclopentane, or cyclohexane ring that is fused to the phenyl ring;

$R^3$ is a lone pair of electrons, $C_1-C_{10}$ alkyl, $C_2-C_{10}$ alkenyl, arylalkyl, (heteroaryl)alkyl, (cycloalkyl)alkyl, arylalkenyl, diarylalkyl or —$(CH_2)_m$—A—$(CH_2)_n$—Q;

m is 1 to 6 and n is 0 to 6;

A is —O—, —S—, —$NR^{4+}$, C=O, or a single bond;

Q is phenyl substituted with $R^7$ or naphthyl substituted with $R^7$;

R[7] is hydrogen, $C_1$–$C_6$ alkyl, $C_1$–$C_6$ alkoxy, hydroxy, halogen, amino, di($C_1$–$C_6$ alkyl)amino, nitro, $C_1$–$C_6$ thioalkoxy, aryl, heteroaryl, aryloxy, —CO-aryl or arylthio;

R[4] and R[5] are each independently hydrogen, $C_1$–$C_6$ alkyl or —NR[4]R[5] represents a 5-, 6-, or 7-membered ring containing nitrogen; and R[6] is hydrogen, $C_1$–$C_6$ alkyl, $C_1$–$C_6$ alkoxy, hydroxy, halogen, amino, di($C_1$–$C_6$ alkyl)amino, nitro or $C_1$–$C_6$ thioalkoxy;

B is a linking moiety or a bond; and

C is a therapeutic agent.

6. The method of claim 5 wherein

X=Y is C=C or N=N;

R[1] and R[2] are each independently hydrogen, $C_1$–$C_6$ alkyl, $C_1$–$C_6$ alkoxy, halogen, nitro, $C_1$–$C_6$ thioalkoxy, or R[1] and R[2] combined form a benzene, cyclopentane, or cyclohexane ring that is fused to the phenyl ring;

R[3] is $C_1$–$C_{10}$ alkyl, $C_2$–$C_{10}$ alkenyl, arylalkyl, (cycloalkyl)alkyl, arylalkenyl, diarylalkyl, or —(CH$_2$)$_m$—A—(CH$_2$)$_n$—Q;

m is 1 to 5 and n is 0 to 4;

A is —O—, —S—, or a single bond;

Q is phenyl substituted with R[7] or naphthyl substituted with R[7];

R[7] is hydrogen, $C_1$–$C_6$ alkyl, $C_1$–$C_6$ alkoxy, hydroxy, halogen, amino, di($C_1$–$C_6$ alkyl)amino, nitro, $C_1$–$C_6$ thioalkoxy, aryl, aryloxy, —CO-aryl, or arylthio;

R[4] and R[5] are each independently hydrogen or $C_1$–$C_6$ alkyl; and

R[6] is hydrogen, $C_1$–$C_6$ alkyl, or halogen.

7. The method of claim 5 wherein

X=Y is C=C or N=N;

R[1] and R[2] are each independently hydrogen, $C_1$–$C_6$ alkyl, $C_1$–$C_6$ alkoxy, halogen, nitro, or R[1] and R[2] combined form a (4,5), (5,6), or (6,7) benzene ring that is fused to the phenyl ring;

R[3] is $C_1$–$C_{10}$ alkyl, $C_2$–$C_{10}$ alkenyl, arylalkyl, arylalkenyl, diarylalkyl, or —(CH$_2$)$_m$—A—(CH$_2$)$_n$—Q;

m is 2 to 4 and n is 0 to 3;

A is —O—, or a single bond;

Q is phenyl substituted with R[7] or naphthyl substituted with R[7];

R[7] is hydrogen, $C_1$–$C_6$ alkyl, $C_1$–$C_6$ alkoxy, hydroxy, halogen, aryl, aryloxy, or —CO-aryl;

R[4] and R[5] are each independently hydrogen, methyl, ethyl, n-propyl or n-butyl; and R[6] is hydrogen or halogen.

8. The method of claim 5 wherein the patient has Alzheimer's disease or Down's syndrome.

9. The method of claim 5 wherein the linking moiety is a covalent bond, amino acids, peptide, alkyl chain, hydroxy acid, or diacid.

10. A method of inhibiting the aggregation of amyloid proteins to form amyloid deposits, the method comprising:
   a. administering to a patient an amyloid protein aggregation inhibiting amount of a compound of Formula I or a pharmaceutically acceptable salt, ester, or amide thereof

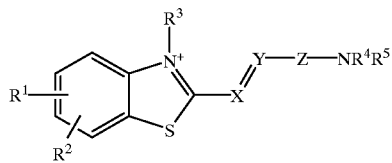

wherein

X and Y are each independently C or N and the X=Y double bond has the trans configuration;

Z is

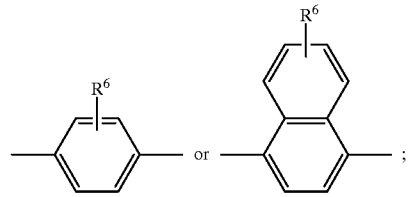

R[1] and R[2] are each independently hydrogen, $C_1$–$C_6$ alkyl, $C_1$–$C_6$ alkoxy, hydroxy, halogen, amino, di($C_1$–$C_6$ alkyl)amino, mono($C_1$–$C_6$ alkyl)amino, nitro, $C_1$–$C_6$ thioalkoxy or R[1] and R[2] combined form a benzene, cyclopentane, or cyclohexane ring that is fused to the phenyl ring;

R[3] is a lone pair of electrons, $C_1$–$C_{10}$ alkyl, $C_2$–$C_{10}$ alkenyl, arylalkyl, (heteroaryl)alkyl, (cycloalkyl)alkyl, arylalkenyl, diarylalkyl, or —(CH$_2$)$_m$—A—(CH$_2$)$_n$—Q;

m is 1 to 6 and n is 0 to 6;

A is —O—, —S—, —NR[4], C=O, or a single bond;

Q is phenyl substituted with R[7] or naphthyl substituted with R[7];

R[7] is hydrogen, $C_1$–$C_6$ alkyl, $C_1$–$C_6$ alkoxy, hydroxy, halogen, amino, di($C_1$–$C_6$ alkyl)amino, nitro, $C_1$–$C_6$ thioalkoxy, aryl, heteroaryl, aryloxy, —CO-aryl, or arylthio;

R[4] and R[5] are each independently hydrogen, $C_1$–$C_6$ alkyl or —NR[4]R[5] represents a 5-, 6- or 7-membered ring containing nitrogen; and R[6] is hydrogen, $C_1$–$C_6$ alkyl, $C_1$–$C_6$ alkoxy, hydroxy, halogen, amino, di($C_1$–$C_6$ alkyl)amino, nitro, or $C_1$–$C_6$ thioalkoxy.

11. The method of claim 10 wherein

X=Y is C=C or N=N;

R[1] and R[2] are each independently hydrogen, $C_1$–$C_6$ alkyl, $C_1$–$C_6$ alkoxy, halogen, nitro, $C_1$–$C_6$ thioalkoxy, or R[1] and R[2] combined form a benzene, cyclopentane, or cyclohexane ring that is fused to the phenyl ring;

R[3] is $C_1$–$C_{10}$ alkyl, $C_2$–$C_{10}$ alkenyl, arylalkyl, (cycloalkyl)alkyl, arylalkenyl, diarylalkenyl, or —(CH$_2$)$_m$—A—(CH$_2$)$_n$—Q;

m is 1 to 5 and n is 0 to 4;

A is —O—, —S—, or a single bond;

Q is phenyl substituted with R[7] or naphthyl substituted with R[7];

R[7] is hydrogen, $C_1$–$C_6$ alkyl, $C_1$–$C_6$ alkoxy, hydroxy, halogen, amino, di($C_1$–$C_6$ alkyl)amino, nitro, $C_1$–$C_6$ thioalkoxy, aryl, aryloxy, —CO-aryl, or arylthio;

R[4] and R[5] are each independently hydrogen or $C_1$–$C_6$ alkyl; and $R^6$ is hydrogen, $C_1$–$C_6$ alkyl, or halogen.

12. The method of claim 10 wherein

X=Y is C=C or N=N;

$R^1$ and $R^2$ are each independently hydrogen, $C_1$–$C_6$ alkyl, $C_1$–$C_6$ alkoxy, halogen, nitro, or $R^1$ and $R^2$ combined form a (4,5), (5,6), or (6,7) benzene ring that is fused to the phenyl ring;

$R^3$ is $C_1$–$C_{10}$ alkyl, $C_2$–$C_{10}$ alkenyl, arylalkyl, arylalkenyl, diarylalkyl, or —(CH$_2$)$_m$—A—(CH$_2$)$_n$—Q;

m is 2 to 4 and n is 0 to 3;

A is —O—, or a single bond;

Q is phenyl substituted with $R^7$ or naphthyl substituted with $R^7$;

$R^7$ is hydrogen, $C_1$–$C_6$ alkyl, $C_1$–$C_6$ alkoxy, hydroxy, halogen, aryl, aryloxy, or —CO-aryl;

$R^4$ and $R^5$ are each independently hydrogen, methyl, ethyl, n-propyl or n-butyl; and $R^6$ is hydrogen or halogen.

13. A method for determining a compound's ability to inhibit the aggregation of amyloid proteins, the method comprising:

a. combining solutions of the compound and amyloid proteins;

b. introducing into the solution a labeled compound of Formula I or a pharmaceutically acceptable salt, ester, or amide thereof

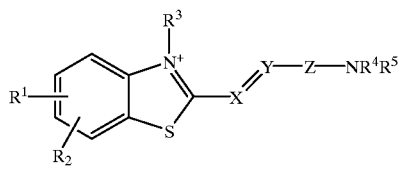

I wherein

X and Y are each independently C or N and the X=Y double bond has the trans configuration;

Z is

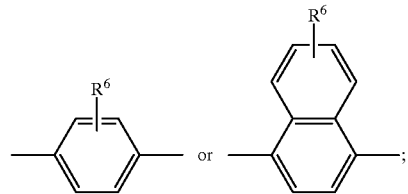

$R^1$ and $R^2$ are each independently hydrogen, $C_1$–$C_6$ alkyl, $C_1$–$C_6$ alkoxy, hydroxy, halogen, amino, di($C_1$–$C_6$ alkyl)amino, mono($C_1$–$C_6$ alkyl)amino, nitro, $C_1$–$C_6$ thioalkoxy, or $R^1$ and $R^2$ combined form a benzene, cyclopentane, or cyclohexane ring that is fused to the phenyl ring;

$R^3$ is a lone pair of electrons, $C_1$–$C_{10}$ alkyl, $C_2$–$C_{10}$ alkenyl, arylalkyl, (heteroaryl)alkyl, (cycloalkyl)alkyl, arylalkenyl, diarylalkyl, or —(CH$_2$)$_m$—A—(CH$_2$)$_n$—Q;

m is 1 to 6 and n is 0 to 6;

A is —O—, —S—, —NR$^4$, C=O, or a single bond;

Q is phenyl substituted with $R^7$ or naphthyl substituted with $R^7$;

$R^7$ is hydrogen, $C_1$–$C_6$ alkyl, $C_1$–$C_6$ alkoxy, hydroxy, halogen, amino, di($C_1$–$C_6$ alkyl)amino, nitro, $C_1$–$C_6$ thioalkoxy, aryl, heteroaryl, aryloxy, —CO-aryl, or arylthio;

$R^4$ and $R^5$ are each independently hydrogen, $C_1$–$C_6$ alkyl or —NR$^4$R$^5$ represents a 5-, 6- or 7-membered ring containing nitrogen; and $R^6$ is hydrogen, $C_1$–$C_6$ alkyl, $C_1$–$C_6$ alkoxy, hydroxy, halogen, amino, di($C_1$–$C_6$ alkyl)amino, nitro, or $C_1$–$C_6$ thioalkoxy;

c. filtering or centrifuging the solution; and d. determining the amount of labeled compound in the filtrate or supernatant.

14. The method of claim 13 wherein

X=Y is C=C or N=N;

$R^1$ and $R^2$ are each independently hydrogen, $C_1$–$C_6$ alkyl, $C_1$–$C_6$ alkoxy, halogen, nitro, $C_1$–$C_6$ thioalkoxy, or $R^1$ and $R^2$ combined form a benzene, cyclopentane, or cyclohexane ring that is fused to the phenyl ring;

$R^3$ is $C_1$–$C_{10}$ alkyl, $C_2$–$C_{10}$ alkenyl, arylalkyl, (cycloalkyl)alkyl, arylalkenyl, diarylalkenyl, or —(CH$_2$)$_m$—A—(CH$_2$)$_n$—Q;

m is 1 to 5 and n is 0 to 4;

A is —O—, —S—, or a single bond;

Q is phenyl substituted with $R^7$ or naphthyl substituted with $R^7$;

$R^7$ is hydrogen, $C_1$–$C_6$ alkyl, $C_1$–$C_6$ alkoxy, hydroxy, halogen, amino, di($C_1$–$C_6$ alkyl)amino, nitro, $C_1$–$C_6$ thioalkoxy, aryl, aryloxy, —CO-aryl, or arylthio;

$R^4$ and $R^5$ are each independently hydrogen or $C_1$–$C_6$ alkyl; and $R^6$ is hydrogen, $C_1$–$C_6$ alkyl, or halogen.

15. The method of claim 13 wherein

X=Y is C=C or N=N;

$R^1$ and $R^2$ are each independently hydrogen, $C_1$–$C_6$ alkyl, $C_1$–$C_6$ alkoxy, halogen, nitro, or $R^1$ and $R^2$ combined form a (4,5), (5,6), or (6,7) benzene ring fused to the phenyl group;

$R^3$ is $C_1$–$C_{10}$ alkyl, $C_2$–$C_{10}$ alkenyl, arylalkyl, arylalkenyl, diarylalkyl, or —(CH$_2$)$_m$—A—(CH$_2$)$_n$—Q;

m is 2 to 4 and n is 0 to 3;

A is —O—, or a single bond;

Q is phenyl substituted with $R^7$ or naphthyl substituted with $R^7$;

$R^7$ is hydrogen, $C_1$–$C_6$ alkyl, $C_1$–$C_6$ alkoxy, hydroxy, halogen, aryl, aryloxy, or —CO-aryl;

$R^4$ and $R^5$ are each independently hydrogen, methyl, ethyl, n-propyl, or n-butyl; and $R^6$ is hydrogen or halogen.

16. A compound of the Formula I or a pharmaceutically acceptable salt, ester, or amide thereof

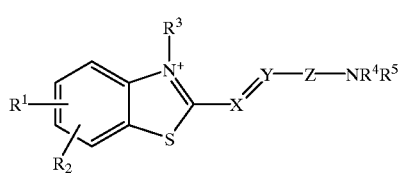

I wherein

X and Y are each independently C or N and the X=Y double bond has the trans configuration;

Z is

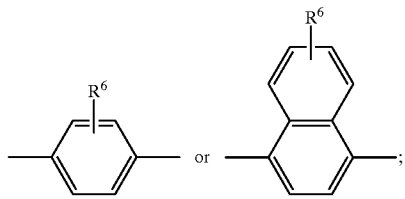

$R^1$ and $R^2$ are each independently hydrogen, $C_1$–$C_6$ alkyl, $C_1$–$C_6$ alkoxy, hydroxy, halogen, amino, di($C_1$–$C_6$ alkyl)amino, mono($C_1$–$C_6$ alkyl)amino, nitro, $C_1$–$C_6$ thioalkoxy, or $R^1$ and $R^2$ combined form a benzene, cyclopentane, or cyclohexane ring that is fused to the phenyl ring;

$R^3$ is a lone pair of electrons, $C_1$–$C_{10}$ alkyl, $C_2$–$C_{10}$ alkenyl, arylalkyl, (heteroaryl)alkyl, di(cycloalkyl) alkyl, arylalkenyl, diarylalkyl, or —(CH$_2$)$_m$—A—(CH$_2$)$_n$—Q;

m is 1 to 6 and n is 0 to 6;

A is —O—, —S—, —NR$^{4\text{-}}$, C=O, or a single bond;

Q is phenyl substituted with $R^7$ or naphthyl substituted with $R^7$;

$R^7$ is hydrogen, $C_1$–$C_6$ alkyl, $C_1$–$C_6$ alkoxy, hydroxy, halogen, amino, di($C_1$–$C_6$ alkyl)amino, nitro, $C_1$–$C_6$ thioalkoxy, aryl, heteroaryl, aryloxy, —CO-aryl, or arylthio;

$R^4$ and $R^5$ are each independently hydrogen, $C_1$–$C_6$ alkyl or —NR$^4$R$^5$ represents a 5-, 6- or 7-membered ring containing nitrogen; and $R^6$ is hydrogen, $C_1$–$C_6$ alkyl, $C_1$–$C_6$ alkoxy, hydroxy, halogen, amino, di($C_1$–$C_6$ alkyl)amino, nitro, or $C_1$–$C_6$ thioalkoxy, and one or more atoms in the compound has been replaced with a radioisotope.

17. The compound of claim 16 wherein the radioisotope is $^3$H, $^{123}$I, $^{128}$I, $^{131}$I, $^{35}$S, $^{11}$C, $^{15}$O, or $^{18}$F.

* * * * *

UNITED STATES PATENT AND TRADEMARK OFFICE
CERTIFICATE OF CORRECTION

PATENT NO. : 6,001,331
DATED : Dec. 14, 1999
INVENTOR(S) : Caprathe et al.

It is certified that error appears in the above-identified patent and that said Letters Patent is hereby corrected as shown below:

Column 29, line 46, "—NR⁴—" should read "—NR⁴—".

Column 32, line 1, "Dibethylaminophenyl" should read "Dibutylaminophenyl".

Column 32, line 65, "—NR⁴—" should read "—NR⁴—".

Column 34, line 36, "—NR⁴" should read "—NR⁴—".

Column 35, line 65, "—NR⁴" should read "—NR⁴—".

Column 38, line 2, "—NR⁴—" should read "—NR⁴—".

Column 29, line 43, "—A—(CH2)ₙ" should read "—A—(CH₂)ₙ".

Column 37, line 20, delete "di" before "(cycloalkyl)".

Signed and Sealed this

Twenty-sixth Day of September, 2000

Attest:

Q. TODD DICKINSON

*Attesting Officer*  *Director of Patents and Trademarks*